(12) United States Patent
Toda et al.

(10) Patent No.: US 12,090,172 B2
(45) Date of Patent: Sep. 17, 2024

(54) SUICIDE GENE THERAPEUTIC AGENT FOR BRAIN TUMORS USING PLURIPOTENT STEM CELL

(71) Applicant: KEIO UNIVERSITY, Tokyo (JP)

(72) Inventors: Masahiro Toda, Tokyo (JP); Hideyuki Okano, Tokyo (JP); Hiroyuki Miyoshi, Tokyo (JP); Ryota Tamura, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 1129 days.

(21) Appl. No.: 16/765,257

(22) PCT Filed: Nov. 19, 2018

(86) PCT No.: PCT/JP2018/042629
§ 371 (c)(1),
(2) Date: May 19, 2020

(87) PCT Pub. No.: WO2019/098361
PCT Pub. Date: May 23, 2019

(65) Prior Publication Data
US 2021/0369785 A1    Dec. 2, 2021

(30) Foreign Application Priority Data
Nov. 20, 2017 (JP) ................................ 2017-223202

(51) Int. Cl.
| | |
|---|---|
| *A61K 35/30* | (2015.01) |
| *A61K 31/513* | (2006.01) |
| *A61P 35/00* | (2006.01) |
| *C12N 5/0797* | (2010.01) |
| *C12N 9/10* | (2006.01) |
| *C12N 9/78* | (2006.01) |
| *C12N 15/63* | (2006.01) |

(52) U.S. Cl.
CPC ............ *A61K 35/30* (2013.01); *A61K 31/513* (2013.01); *A61P 35/00* (2018.01); *C12N 5/0623* (2013.01); *C12N 9/1077* (2013.01); *C12N 9/78* (2013.01); *C12N 15/635* (2013.01); *C12Y 204/02009* (2013.01); *C12Y 305/04001* (2013.01); *C12N 2506/45* (2013.01)

(58) Field of Classification Search
CPC .... A61K 35/30; C12N 5/0623; C12N 15/635; C12N 2506/45
See application file for complete search history.

(56) References Cited

FOREIGN PATENT DOCUMENTS

| EP | 3 622 961 A1 | 3/2020 |
| WO | WO 2017/079673 A1 | 5/2017 |
| WO | WO 2018/207808 A1 | 11/2018 |

OTHER PUBLICATIONS

Altanerova et al., "Human adipose tissue-derived mesenchymal stem cells expressing yeast cytosinedeaminase::uracil phosphoribosyltransferase inhibit intracerebral rat glioblastoma," International Journal of Cancer, vol. 130, 2012, pp. 2455-2463, 9 pages total.
Bagó et al., "Neural stem cell therapy for cancer," Methods, vol. 99, 2015, pp. 37-43, 7 pages total.
Extended European Search Report for European Application No. 18878961.4, dated Jun. 11, 2021.
Wen et al., "Production of neural stem cells from human pluripotent stem cells," Journal of Biotechnology, vol. 188, 2014, pp. 122-129, 8 pages total.
Aboody et al., "Neural stem cells display extensive tropism for pathology in adult brain: Evidence from intracranial gliomas", PNAS, Nov. 7, 2000, vol. 97, No. 23, pp. 12846-12851.
Altaner, "Prodrug gene therapy for cancer mediated by mesenchymal stem/stromal cells engineered to express yeast cytosinedeaminase:: Uracilphosphoribosyltransferase", J Stem Cell Res Ther, 2015, vol. 5, Issue. 2, article No. 1000264, total 5 pages.
International Search Report, issued in PCT/JP2018/042629, dated Jan. 8, 2019.
Kalimuthu et al., "Tet-On regulating HSV-sr39tk suicide gene expressing mesenchymal stem cells with dual reporter system exert bystander effect on anaplastic thyroid cancer", J Nucl Med, May 1, 2016, vol. 57, Supplement 2, Abstract, No. 1397, total 2 pages.
Kao et al., "GAPTrap: a simple expression system for pluripotent stem cells and their derivatives", Stem Cell Reports, Sep. 13, 2016, vol. 7, pp. 518-526.
Kim et al., "Therapeutic effect of genetically modified human neural stem cells encoding cytosine deaminase on experimental glioma", Biochemical and Biophysical Research Communications, 2012, vol. 417, pp. 534-540.
Lee et al., "Glioma gene therapy using induced pluripotent stem cell derived neural stem cells", Molecular Pharmaceutics, 2011, vol. 8, pp. 1515-1524.
Meca-Cortés et al., "CRISPR/cas9-mediated knockin application in cell therapy: A non-viral procedure for bystander treatment of glioma in mice", Molecular Therapy Nucleic Acids, Sep. 2017, vol. 8, pp. 395-403.
Wang et al., "Neural stem cell-based dual suicide gene delivery for metastatic brain tumors" Program abstracts of the 21st Annual Meeting of the Japanese Society Cell Death Research, 2012, p. 57, Abstract P-08, entire text, non-official translation.
Written Opinion of the International Searching Authority, issued in PCT/JP2018/042629, dated Jan. 8, 2019.
Zeng et al., "The cell death and DNA damages caused by the Tet-On regulating HSV-tk/GCV suicide gene system in MCF-7 cells", Biomedicine & Pharmacotherapy, 2014, vol. 68, pp. 887-892.

(Continued)

*Primary Examiner* — Mark Halvorson
*Assistant Examiner* — Dennis J Sullivan
(74) *Attorney, Agent, or Firm* — Birch, Stewart, Kolasch & Birch, LLP

(57) ABSTRACT

A cell preparation for treating brain tumors used in combination with a prodrug that is converted to 5-fluorouracil by cytosine deaminase, wherein the cell preparation comprises neural stem cells derived from pluripotent stem cells having a cytosine deaminase gene and a uracil phosphoribosyltransferase gene is provided to establish new means for treating brain tumors.

10 Claims, 17 Drawing Sheets

(56) References Cited

OTHER PUBLICATIONS

International Preliminary Report on Patentability (Form PCT/IB/373) with English translation of the Written Opinion issued May 26, 2020 in PCT/JP2018/042629.

SUICIDE GENE THERAPEUTIC AGENT FOR BRAIN TUMORS USING PLURIPOTENT STEM CELL

TECHNICAL FIELD

The present invention relates to a cell preparation for treating brain tumors and a method for preparing neural stem cells used for the cell preparation.

BACKGROUND ART

Malignant gliomas are very difficultly treated in the present therapies due to treatment resistance by brain tumor stem cells (BTSCs), which infiltrate the brain substance widely. Since suicide gene therapies using viral vectors exerted bystander effects, the effectiveness was expected. Since the diffusion among infiltrating tumor cells was insufficient, the results of the clinical tests were however limited. It has been revealed recently that neural stem cells (NSCs) have the properties of migrating and accumulating in brain tumor stem cells, and attempts to apply neural stem cells to suicide gene treatment as cell vehicles attract attention, and a technique as to suicide gene treatment using mesenchymal stem cells, which has properties similar to neural stem cells has been developed (Patent Literature 1).

CITATION LIST

Patent Literature

Patent Literature 1:
  Japanese Patent Laid-Open No. 2006-345726

SUMMARY OF INVENTION

Technical Problem

Although great expectations have been placed on suicide gene treatment using neural stem cells or mesenchymal stem cells as mentioned above, it is difficult, including ethical issues, to obtain an adequate amount of neural stem cells which can be administered to humans clinically. It is easier to obtain mesenchymal stem cells than neural stem cells. As long as mesenchymal stem cells are collected from the living body, the amount thereof collected is however limited.

The herpes simplex virus thymidine kinase gene (HSVtk) is generally used as a suicide gene (for example, this gene is used in Examples in Patent Literature 1), and besides this, the cytosine deaminase (CD) gene and the uracil phosphoribosyltransferase (UPRT) gene are known. It is known that even though the CD gene and the UPRT gene are used alone, the CD gene and the UPRT gene have antitumor effects, and the antitumor effect improves synergistically by combining the two (a gene into which these two genes are combined may be called a "CD-UPRT gene" hereinafter).

An object of the present invention is to solve the difficulty of obtaining neural stem cells and mesenchymal stem cells, which is problematic, in such a context and to provide new means for treating brain tumors using the CD-UPRT gene, which has a high antitumor effect.

Solution to Problem

The present inventor has earnestly examined repeatedly to solve the above-mentioned problem and consequently found that inducing the differentiation of neural stem cells from iPS cells enables obtaining neural stem cells in an amount enough to be used for a suicide gene therapy. It has been found that CD-UPRT gene-expressing neural stem cells which are excellent in safety, quality control, and stable supply properties can be obtained by inserting the CD-UPRT gene into the region of a housekeeping gene of iPS cells by genome editing. Furthermore, it has been found that these CD-UPRT gene-expressing neural stem cells exhibit an antitumor effect not only on brain tumor cells but also on brain tumor stem cells.

The present invention has been completed based on the above knowledge.

That is, the present invention provides the following [1] to [17].

[1] A cell preparation for treating brain tumors used in combination with a prodrug that is converted to 5-fluorouracil by cytosine deaminase, wherein the cell preparation comprises neural stem cells derived from pluripotent stem cells having a cytosine deaminase gene and a uracil phosphoribosyltransferase gene.

[2] The cell preparation for treating brain tumors according to [1], wherein the prodrug that is converted to 5-fluorouracil by cytosine deaminase is 5-fluorocytosine.

[3] The cell preparation for treating brain tumors according to [1] or [2], wherein the neural stem cells derived from pluripotent stem cells are neural stem cells obtained by performing the following step (1) and then performing the following step (2):
  (1) introducing a cytosine deaminase gene and a uracil phosphoribosyltransferase gene into pluripotent stem cells,
  (2) differentiating the pluripotent stem cells into neural stem cells.

[4] The cell preparation for treating brain tumors according to [3], wherein the cytosine deaminase gene and the uracil phosphoribosyltransferase gene are inserted into the genome of the pluripotent stem cells by genome editing.

[5] The cell preparation for treating brain tumors according to [4], wherein the cytosine deaminase gene and the uracil phosphoribosyltransferase gene are inserted into a region of a housekeeping gene or AAVS1 region of the pluripotent stem cells.

[6] The cell preparation for treating brain tumors according to [5], wherein the housekeeping gene is a glyceraldehyde-3-phosphate dehydrogenase gene.

[7] The cell preparation for treating brain tumors according to [3], wherein the cytosine deaminase gene and the uracil phosphoribosyltransferase gene are a gene structure, expression of which can be regulated artificially.

[8] The cell preparation for treating brain tumors according to [7], wherein the gene structure is a gene structure expressed by addition of doxycycline.

[9] The cell preparation for treating brain tumors according to [1] or [2], wherein the neural stem cells derived from pluripotent stem cells are neural stem cells obtained by performing the following step (1) and then performing the following step (2):
  (1) differentiating pluripotent stem cells into neural stem cells,
  (2) introducing a cytosine deaminase gene and a uracil phosphoribosyltransferase gene into the neural stem cells.

[10] The cell preparation for treating brain tumors according to any one of [1] to [9], wherein the pluripotent stem cells are iPS cells.

[11] A method for preparing neural stem cells having a cytosine deaminase gene and a uracil phosphoribosyltransferase gene, the method being a method comprising performing the following step (A1) and then performing the following step (A2), or a method comprising performing the following step (B1) and then performing the following step (B2):

(A1) introducing a cytosine deaminase gene and a uracil phosphoribosyltransferase gene into pluripotent stem cells, (A2) differentiating the pluripotent stem cells into neural stem cells, (B1) differentiating pluripotent stem cells into neural stem cells, (B2) introducing a cytosine deaminase gene and a uracil phosphoribosyltransferase gene into the neural stem cells.

[12] The method for preparing neural stem cells according to [11], wherein the cytosine deaminase gene and the uracil phosphoribosyltransferase gene are inserted into the genome of the pluripotent stem cells by genome editing in the step (A1).

[13] The method for preparing neural stem cells according to [12], wherein the cytosine deaminase gene and the uracil phosphoribosyltransferase gene are inserted into a region of a housekeeping gene or AAVS1 region of the pluripotent stem cells in the step (A1).

[14] The method for preparing neural stem cells according to [13], wherein the housekeeping gene is a glyceraldehyde-3-phosphate dehydrogenase gene.

[15] The method for preparing neural stem cells according to [11], wherein the cytosine deaminase gene and the uracil phosphoribosyltransferase gene are a gene structure, expression of which can be regulated artificially, in the step (A1).

[16] The method for preparing neural stem cells according to [15], wherein the gene structure is a gene structure expressed by addition of doxycycline.

[17] The method for preparing neural stem cells according to any one of [11] to [16], wherein the pluripotent stem cells are iPS cells.

The present specification includes contents described in the description and/or the drawings of Japanese Patent Application No. 2017-223202, which is the basis of the priority of the present application.

Advantageous Effects of Invention

The present invention provides new means for treating brain tumors using neural stem cells derived from pluripotent stem cells such as iPS cells and ES cells.

DESCRIPTION OF EMBODIMENTS

Figure 1:
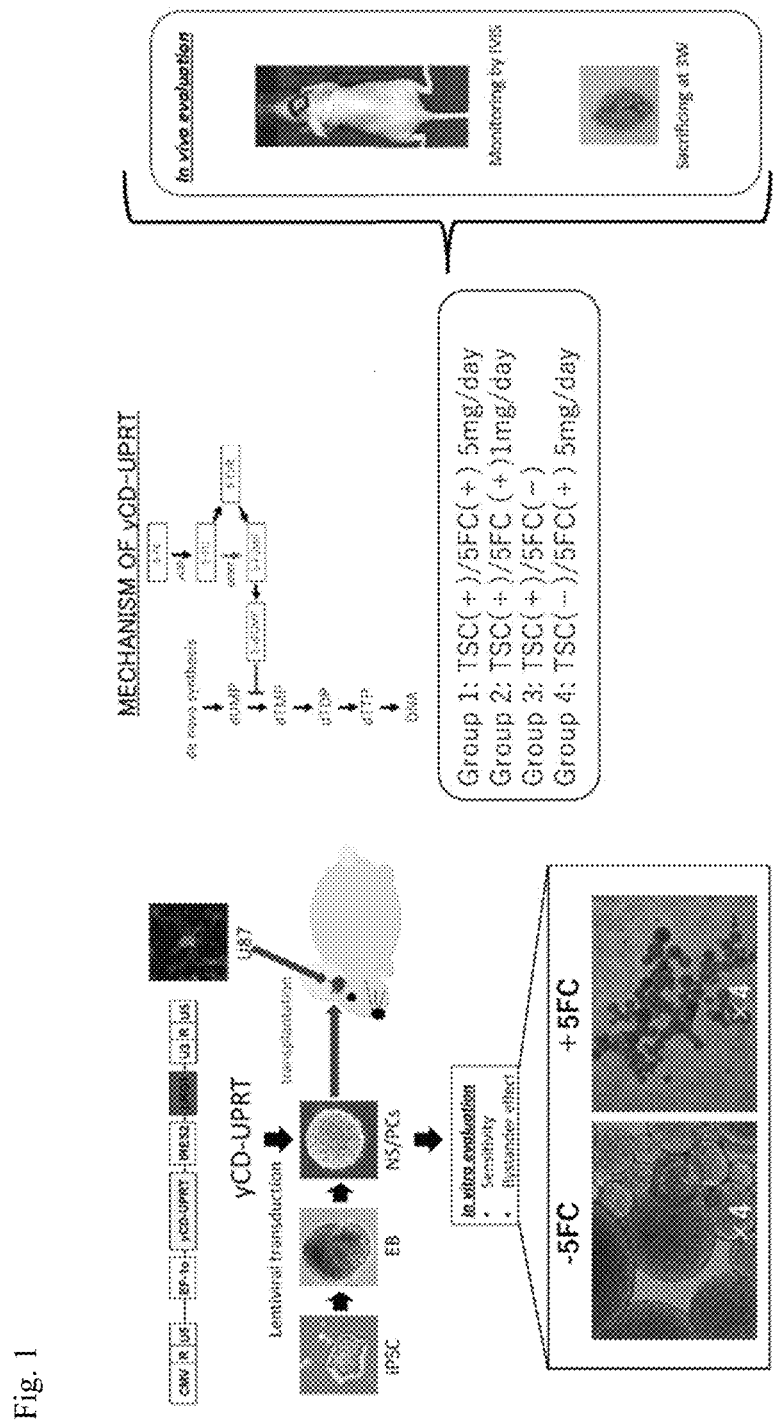
FIG. 1 shows the summary of a suicide gene cell therapy for malignant brain tumors using therapeutic stem cells (TSCs) expressing yCD-UPRT (mixture transplantation model).

The present invention will be described in detail hereinafter.

A cell preparation for treating brain tumors of the present invention is a cell preparation for treating brain tumors used in combination with a prodrug that is converted to 5-fluorouracil by cytosine deaminase (CD), wherein the cell preparation comprises neural stem cells derived from pluripotent stem cells having a cytosine deaminase gene and a uracil phosphoribosyltransferase gene (CD-UPRT gene).

The "pluripotent stem cells" in the present invention can be interpreted as a meaning which those skilled in the art usually use, and include, for example, iPS cells and ES cells.

The "brain tumors" in the present invention means tumors which are developed in intracranial tissue. Specific examples thereof include gliomas, medulloblastomas, neuroblastomas, meningiomas, pituitary adenomas, neurinomas, primary central nervous system lymphomas, sarcomas and spinal cord tumors. In the present invention, although all of these brain tumors can be objects to be treated, it is preferable that gliomas be objects to be treated.

The "treatment" in the present invention means not only killing tumor cells but also reducing tumor cells or inhibiting the proliferation of tumor cells.

A CD gene and a UPRT gene are suicide genes having 5-fluorocytosine (5-FC) and 5-fluorouracil (5-FU) as prodrugs, respectively. Vectors which express these suicide genes are sold on the market, and pluripotent stem cells and neural stem cells which express these suicide genes can be prepared using such vectors. It is known that even though the CD gene and the UPRT gene are used alone, the CD gene and the UPRT gene have antitumor effect, and around 100 times higher antitumor effect is obtained by introducing these two genes into cells than when the CD gene is introduced alone.

As long as the prodrug in the present invention is converted to 5-FU by CD, the prodrug may be any prodrug. Although examples of such a prodrug include 5-FC, the prodrug is not limited to this.

The "neural stem cells" in the present invention means stem cells having the capability to supply cells which differentiates into neurons and glia cells. The cell preparation of the present invention contains these neural stem cells. As long as the cell preparation does not exert a great adverse influence on the effect of treating brain tumors, the cell preparation may contain cells other than neural stem cells. When neural stem cells are prepared from iPS cells in accordance with a method described in the below-mentioned Mol Brain 9: 85, 2016, not only neural stem cells but also neural precursor cells are produced. For this reason, the cell preparation of the present invention may contain both neural stem cells and neural precursor cells. Neural stem cells used in the present invention is neural stem cells derived from pluripotent stem cell such as iPS cells, and neural stem cells collected from the brain or the like is not used as they are.

Neural stem cells derived from pluripotent stem cells having a CD-UPRT gene can be prepared by a method including performing a step (A1) and then performing a step (A2), or a method including performing a step (B1) and then performing a step (B2) described below.

In the step (A1), the CD-UPRT gene is introduced into pluripotent stem cells.

Although ES cells can also be used as the pluripotent stem cells, it is preferable to use iPS cells. As long as iPS cells to be used can be differentiated into neural stem cells, the origin thereof, a reprogramming factor to be introduced, a method for introducing a reprogramming factor and the like are not particularly limited. Since the cell preparation of the present invention is used mainly for treating human brain tumors, it is however preferable to use iPS cells derived from a human in such a case. In this case, iPS cells derived from a patient to whom the cell preparation is administered may be used, and iPS cells derived from a human other than the patient may be used. As mentioned above, although a method for introducing a reprogramming factor is not limited, either, it is preferable to use integration-free iPS cells. Although iPS cells to be used may be prepared in accordance with a well-known method, iPS cells can also be obtained from research institutions such as the Center for iPS Cell Research and Application (CiRA), Kyoto University.

Although the CD-UPRT gene may be introduced into the pluripotent stem cells using a viral vector, the CD-UPRT gene is preferably introduced into the pluripotent stem cells using genome editing. When the suicide gene is inserted into the genome of the pluripotent stem cells using a viral vector such as a lentiviral vector, the suicide gene is inserted into chromosomes at random, and the gene variations of the insertion sites, the activation of peripheral genes and the inactivation of the suicide gene by positional effect are therefore concerned. It is considered that using not a viral vector but genome editing enables avoiding such a problem.

The genome can be edited using ZFN, TALEN, CRISPR/Cas9 or the like, and it is preferable to edit the genome using CRISPR/Cas9 among these. It is preferable to insert the CD-UPRT gene into the region of a housekeeping gene of the pluripotent stem cells by genome editing. As long as the housekeeping gene is expressed in a certain amount in many cells, the housekeeping gene is not particularly limited. Specific examples thereof include a glyceraldehyde-3-phosphate dehydrogenase (GAPDH) gene, a cyclophilin gene, a β-actin gene and an α-tubulin gene, and the GAPDH gene is preferable among these. The CD-UPRT gene may be inserted into AAVS1 region of the pluripotent stem cells. Adeno-associated viruses (AAVs) do not have pathogenicity to humans, and the AAVS1 region is considered to be a genome region into which foreign genes are inserted highly safely.

When the CD-UPRT gene is introduced into the pluripotent stem cells using a viral vector, as mentioned above, harmful influence due to random insertion into chromosomes can be considered. Therefore, the CD-UPRT gene is preferably a gene structure, the expression of which can be regulated artificially. Such a gene structure can be produced using a tetracycline-induced system (PLoS One 8:e59890, 2013), which is a well-known expression-inducing system. This tetracycline induction system comprises a region which expresses a reverse tetracycline-controlled transactivator (rtTA), a gene of interest and a region including a TRE promoter disposed upstream thereof. The rtTA bonds to the TRE promoter by bonding to tetracycline and induces the expression of the gene of interest disposed downstream. Using this system enables inducing the expression of the suicide gene by the addition of tetracycline. Although the expression in this system can also be induced with tetracycline as mentioned above, but is usually induced with doxycycline, which is a derivative of tetracycline. The gene structure in which the expression of the CD-UPRT gene can be regulated artificially can also be produced using various induced promoters such as drug-induced promoters besides this tetracycline-induced system.

Examples of the viral vector include adenovirus vectors, adeno-associated viral vectors, retroviral vectors and lentiviral vectors. Among these, a vector which incorporates a gene into the genome is preferable, and a lentiviral vector is most preferable. The sequences of a reporter gene, an IRES or the like may be included in the vector besides the CD-UPRT gene.

In a step (A2), pluripotent stem cells are differentiated into neural stem cells.

Differentiation from pluripotent stem cells to neural stem cells may be performed in accordance with either of well-known methods of a method for preparation through embryoid bodies and a method for preparation without forming embryoid bodies. When differentiation from iPS cells is performed, the differentiation from the iPS cells can be performed, for example, in accordance with the method described in Stem Cell Reports. 2017 Nov. 14; 9(5):1675-1691. According to the above-mentioned method, embryoid bodies can be formed from iPS cells using well-known embryoid body-forming medium, and the embryoid body medium contains a TGFβ family inhibitor (for example, SB431542) and a BMP inhibitor (for example, LDN-193189).

Differentiation from the embryoid bodies to neural stem cells can be performed using well-known neurosphere medium. For example, the neurosphere medium contains an epidermal growth factor and a fibroblast growth factor-2, a leukemia inhibitory factor, a B-27 supplement and the like. Culturing the embryoid bodies in the neurosphere medium forms cell masses called neurospheres and containing neural stem cells. The formed neurospheres are collected and disassembled into single cells. The single cells are cultured in neurosphere medium to form neurospheres again. Such operation is repeated several times, and neural stem cells can be obtained by collecting neurospheres.

When neural stem cells derived from pluripotent stem cells having the CD-UPRT gene are prepared by sequentially performing the steps (A1) and (A2), there is the advantage of neural stem cells for treatment being able to be supplied steadily by proliferating pluripotent stem cells.

In the step (B1), pluripotent stem cells are differentiated into neural stem cells.

The differentiation from pluripotent stem cells to neural stem cells in the step (B1) can be performed in the same way as the differentiation in the step (A2).

In the step (B2), a CD-UPRT gene is introduced into neural stem cells.

The introduction of a CD-UPRT gene into neural stem cells in a step (B2) can be performed in the same way as the introduction in the step (A1). Note that since a problem with cytotoxicity may occur in the step (A1), it is preferable that genome editing be used, and the CD-UPRT gene be a gene structure, the expression of which can be regulated artificially; however, since a problem with cytotoxicity very rarely occurs in the step (B2), these do not usually need to be performed.

As mentioned above, "neural stem cells," which are a "product," are not specified by structure or properties but specified by a preparation method herein. This is because since cells are parts of the living body, the structure and properties thereof are very complicated, and markedly excessive economic expenditure and time are taken to work to specify them.

The cell preparation of the present invention may contain other pharmaceutically acceptable components besides neural stem cells. Examples of such other components include carriers, excipients, disintegrators, buffers, emulsifiers, suspending agents, soothing agents, stabilizers, preservatives, antiseptics and physiological saline solutions. Dimethyl sulfoxide, serum albumin or the like may be contained to protect cells at the time of freeze storage, and an antibiotic or the like may be contained to prevent the contamination and proliferation of bacteria.

The number of neural stem cells contained in the cell preparation of the present invention can be optionally determined in view of the sex, age or weight of a subject, the state of an affected part, the state of cells to be used or the like so as to obtain a desired effect (for example, the disappearance of tumors or the reduction of tumor size) in the treatment of brain tumors.

The cell preparation of the present invention may be administered a plurality of times (for example, 2 to 10 times) at intervals (for example, twice per day, once per day, twice per week, once per week, once per two week). Although the dose can be optionally determined in view of the sex, age or weight of a subject, the state of an affected part, the state of cells to be used or the like, the administration is preferably $1 \times 10^6$ to $1 \times 10^{10}$ cells per individual (human) 1 to 10 times.

The administration site or administration method of the cell preparation of the present invention is not particularly limited. Examples of the administration method include tumor local administration, intracarotidarterial administration and intravenous administration.

The administration site or administration method of a prodrug used in combination with the cell preparation of the present invention is not particularly limited, either. Examples of the administration method also include intraperitoneal administration besides tumor local administration, intracarotidarterial administration and intravenous administration mentioned above.

The prodrug may be administered before or after the administration of the cell preparation of the present invention or at the same time as the administration of the cell preparation, but is usually administered in divided doses after the administration of the cell preparation. The dose of the prodrug can be optionally determined in view of the type of prodrug to be used, the sex, age or weight of a subject or the state of an affected part. When 5-FC is administered, 5-FC is preferably administered at 50 to 200 mg/kg per once, 4 times per day for 2 to 3 weeks (28 times to 42 times) per individual (human).

When the tetracycline induction system is used to prevent cytotoxicity, doxycycline is also administered at the time of treatment to express a suicide gene. Examples of a method for administer doxycycline include oral administration, tumor local administration, intracarotidarterial administration, intravenous administration and intraperitoneal administration. Doxycycline may be administered before or after the administration of the cell preparation of the present invention or at the same time as the administration of the cell preparation, but is usually administered after the administration of the cell preparation.

EXAMPLES

Next, although the present invention will be described in more detail by giving Examples, the present invention is not limited to these Examples.

[Example 1] Suicide Gene Cell Therapy for Glioma Cell (A) Material and Method
<Human iPS Cell>

The used human iPS cell (1210B2) was obtained from the Center for iPS Cell Research and Application (CiRA), Kyoto University. Then, 1210B2 was established by a method for introducing a reprogramming factor using an episomal vector for human peripheral blood mononuclear cells (Okita K, Yamakawa T, Matsumura Y, Sato Y, Amano N, Watanabe A, Goshima N, Yamanaka S. An efficient nonviral method to generate integration-free human-induced pluripotent stem cells from cord blood and peripheral blood cells. Stem Cells. 2013 March; 31(3):458-66). Human iPS cells were inoculated on a plastic culture dish coated with iMatrix-511 (produced by Nippi, Incorporated) and subjected to maintenance culture using Stem Fit AK03 or AK03N medium (produced by AJINOMOTO CO., INC.) by a known feeder-free method (Nakagawa M, Taniguchi Y, Senda S, Takizawa N, Ichisaka T, Asano K, Morizane A, Doi D, Takahashi J, Nishizawa M, Yoshida Y, Toyoda T, Osafune K, Sekiguchi K, Yamanaka S. A novel efficient feeder-free culture system for the derivation of human induced pluripotent stem cells. Sci Rep. 2014 Jan. 8; 4:3594).

<Differentiation Induction from Human iPS Cells to Neural Stem/Precursor Cells (NS/PCs)>

Differentiation induction from human iPS cells to NS/PCs was performed by a known method (Sugai K, Fukuzawa R, Shofuda T, Fukusumi H, Kawabata S, Nishiyama Y, Higuchi Y, Kawai K, Isoda M, Kanematsu D, Hashimoto-Tamaoki T, Kohyama J, Iwanami A, Suemizu H, Ikeda E, Matsumoto M, Kanemura Y, Nakamura M, Okano H. Pathological classification of human iPSC-derived neural stem/progenitor cells towards safety assessment of transplantation therapy for CNS diseases. Mol Brain. 2016 Sep. 19; 9(1):85). First, a 10 µM ROCK inhibitor Y276352 (produced by Wako Pure Chemical Industries, Ltd.) was added to medium of iPS cells, the iPS cells were incubated for 1 to 3 hours, then washed with PBS and disassembled into single cells using TrypLE Select (produced by Life Technologies Corporation). The human iPS cells disassembled into the single cells were suspended in EB (embryoid body)-forming medium to which a 10 µM ROCK inhibitor Y276352 was added (10 µM SB431542 and 100 nM LDN-193189 were added to Stem Fit medium to which C liquid was not added), inoculated at a concentration of $9.0 \times 10^3$ cells/75 µl per 1 well of a low adhesive 96 hole-culture plate (Prime Surface 96V, manufactured by Sumitomo Bakelite Co., Ltd.) and cultured. Then, 75 µl of EB-forming media was added 1 day after, a half amount of EB-forming medium was replaced everyday on and after, and the human iPS cells were cultured for 13 to 14 days to obtain EBs. The EBs were collected from each well and cultured in NS (neurosphere) medium (to D-MEM/Ham's F-12 medium (containing HEPES) (produced by Wako Pure Chemical Industries, Ltd.) were added a 20 ng/ml recombination human epidermal growth factor (produced by PeproTech, Inc.), a 20 ng/ml recombination human fibroblast growth factor-2 (produced by PeproTech, Inc.), a $10^3$ units/ml recombination human leukemia inhibitory factor (produced by NACALAI TESQUE, INC.), a 2% B-27 supplement (produced by Thermo Fisher Scientific K.K.) and 1 unit/ml heparin sodium (produced by AY PHARMACEUTICALS CO., LTD.)) for 7 days. The medium was replaced once per 3 or 4 days during culture. Cell masses were collected by a centrifuge, disassembled into single cells using TrypLE Select and suspended in NS medium. The single cells were inoculated into a low adhesive flask (manufactured by Corning Incorporated) at a concentration of $1 \times 10^5$ cells/ml and cultured for 10 days with the medium replaced every 3 to 4 days to obtain primary NS/PCs. Similarly, the primary NS/PCs were collected by the centrifuge, disassembled into single cells using TrypLE Select and suspended in NS medium. The single cells were inoculated into a low adhesive flask at a concentration of $1 \times 10^5$ cells/ml and cultured for 7 to 10 days with the medium replaced every 3 to 4 days to obtain secondary, tertiary, quaternary and quinary NS/PCs.

<Introduction of yCD-UPRT Gene into NS/PCs Using Lentiviral Vector-Therapeutic Stem Cells, TSCs (1)>

Production of yCD-UPRT Expression Lentiviral Vector

The cDNA of the yCD (yest Cytosine Deaminase)-UPRT (Uracil PhosphoRibosyl Transferase) wherein the cDNA was subcloned from the pSELECT-zeo-Fcy::fur plasmid (produced by InvivoGen Corporation) to pENTR/D-TOPO (produced by Thermo Fisher Scientific K.K.) by PCR and the nucleotide sequence of the cDNA was confirmed, was used. The yCD-UPRT cDNA was subcloned to the lentiviral vector plasmids CSIV-EF-RfA-IRES2-hKO1 to obtain CSIV-EF-yCD-UPRT-IRES2-hKO1. CSIV-EF-yCD-UPRT-IRES2-hKO1 was used to produce a lentiviral vector which expresses yCD-UPRT and hKO1 (Humanized Kusabira-Orange fluorescence protein gene) under the EF-1α promoter. The lentiviral vectors were produced by a known method (Miyoshi H, Blomer U, Takahashi M, Gage F H, Verma I M. Development of a self-inactivating lentivirus vector. J Virol. 1998 October; 72(10):8150-7; Kurita R, Suda N, Sudo K, Miharada K, Hiroyama T, Miyoshi H, Tani K, Nakamura Y. Establishment of immortalized human erythroid progenitor cell lines able to produce enucleated red blood cells. PLoS One. 2013; 8(3):e59890; Hashizume O, Ohnishi S, Mito T, Shimizu A, Ishikawa K, Nakada K, Soda M, Mano H, Togayachi S, Miyoshi H, Okita K, Hayashi J. Epigenetic regulation of the nuclear-coded GCAT and SHMT2 genes confers human age-associated mitochondrial respiration defects. Sci Rep. 2015 May 22; 5:10434.)

Preparation of NS/PCs Expressing yCD-UPRT

Secondary to quaternary NS/PCs differentiation-induced from the human iPS cells were collected by a centrifuge, disassembled into single cells using TrypLE Select, suspended in NS medium, inoculated into a low adhesive flask at a concentration of $1 \times 10^5$ cells/ml, infected with a CSIV-EF-yCD-UPRT-IRES2-hKO1 lentiviral vector at an MOI (multiplicity of infection) of 1 to 2 and cultured for 7 days with the medium replaced every 3 to 4 days. The obtained NS/PCs were infected with the CSIV-EF-yCD-UPRT-IRES2-hKO1 lentiviral vector at an MOI of 1 to 2 in the same way again to prepare therapeutic stem cells (TSCs (1)), that is, NS/PCs expressing yCD-UPRT. It was confirmed that the cell death of the NS/PCs expressing yCD-UPRT was induced by adding 1 µg/ml 5-FC (fluorocytosine) to the medium.

<Introduction of yCD-UPRT Gene into GAPDH Gene Region with CRISPR/Cas9-Therapeutic Stem Cells, TSCs (2)>

Preparation of iPS Cells in which yCD-UPRT Gene was Introduced into GAPDH Gene Region A construct for homologous recombination (HR-GAPDH-2A-yCD-UPRT-2A-Bsd) in which GAPDH (glyc eraldehyde-3-phosphate dehydrogenase), yCD-UPRT and Bsd (blasticidin resistance gene) were inserted, being connected by 2A peptide sequences, and an expression vector construct (U6-GAPDH-gRNA4-Cas9) of a gRNA which targets the vicinity to the stop codon of GAPDH and a Cas9 were produced to incorporate yCD-UPRT into a GAPDH gene region using the CRISPR/Cas9 genome editing technique. These constructs were introduced into a human iPS cell line (1210B2) by electroporation, the culture was performed in the presence of blasticidin S, and the cloning was performed. The homologous recombination iPS cell line was confirmed by nucleotide sequence confirmation by the genomic PCR and the genomic sequencing of clones.

Preparation of NS/PCs Expressing yCD-UPRT

Differentiation induction from iPS cells in which yCD-UPRT was incorporated into the GAPDH gene region to NS/PCs was performed to obtain secondary to quinary NS/PCs (TSCs (2)). Culture was performed with 2 μg/ml blasticidin S always added to the medium. It was confirmed that the cell death of the NS/PCs expressing yCD-UPRT was induced by adding 1 μg/ml 5-FC to the medium.

<Preparation of Human Glioma Cell Line U87 Expressing ffLuc>

The human glioma cell line U87 was infected with the ffLuc (fusion gene of Venus fluorescence protein and Luc2 firefly luciferase) expression lentiviral vector (CSII-EF-ffLuc) (Takahashi Y, Tsuji O, Kumagai G, Hara C M, Okano H J, Miyawaki A, Toyama Y, Okano H, Nakamura M. Comparative study of methods for administering neural stem/progenitor cells to treat spinal cord injury in mice. Cell Transplant. 2011; 20(5):727-39). The clones were sorted with a cell sorter to obtain the U87 cell line, which expresses ffLuc highly and steadily.

<Examination of Therapeutic Effect of NS/PCs Expressing yCD-UPRT in Brain Tumor Model Mice>

Suicide Gene Cell Therapy for Malignant Brain Tumor Using Therapeutic Stem Cells, TSCs (1) Expressing yCD-UPRT (mixture transplantation model)

First, $1\times10^5$ cells/2 μl U87-ffLuc and $5\times10^5$ cells/2 μl TSCs (1) expressing yCD-UPRT (yCD-UPRT was introduced into NS/PCs with the lentiviral vector) were mixed and stereotactically transplanted to the right striate body (2 mm away from the anterior fontanel to the right and 3 mm deep from the brain surface) of each T cell-deficient mouse (female BALB/c nude mouse, 20 g, 6 w) subjected to general anesthesia. Then, for 21 days from the next day, 500 μl of 5-FC (10 mg/ml) was intraperitoneally administered once per day for 2 weeks (treated group 1: TSC (+)/5-FC (+) 5 mg/day, n=9). As another group, 100 μl of 5-FC (10 mg/ml) was intraperitoneally administered once per day for 2 weeks (treated group 2: TSC (+)/5-FC 1 mg/day, n=9). Next, 500 μl of 1 M PBS was administered to a control group for 2 weeks in the same way (control group 1: TSC (+)/5-FC (−), n=9). A group to which only U87-ffLuc was transplanted was also generated as another control group, and 500 μl of 5-FC (10 mg/ml) was intraperitoneally administered to this once per day for 2 weeks (control group 2: TSC (−)/5-FC (+) 5 mg/day, n=3). Change in the tumor of the same individual over time was observed with an IVIS, that is, an in vivo imaging system, every week. At the time of photographing with IVIS, 200 μl of 30 mg/ml VivoGlo™ Luciferin was intraperitoneally administered to the individual subjected to isoflurane inhalation anesthesia, and the tumor was photographed for 10 minutes when the peak was reached.

Three mice of each of the treated groups 1 and 2 and the control group 1 were decapitated in the third week after the tumor transplantation, and the actual tumor volumes were measured. The mice were decapitated by perfusing the mice with 4% paraformaldehyde for fixation through the heart. The brain tissues taken out were replaced with 10% and 20% sucrose, and the brain tissues were sliced to a thickness of 20 μm with a microtome. An 8-well dish the wells of which each contain 1 ml of an antifreeze solution was charged with the sections sequentially and stored at −20° C.

The tumor volumes of the brain sections were measured in more detail by staining with HE or observation through a fluorescence microscope since U87 expresses Venus fluorescence protein. It was evaluated by fluorescently staining the brain tissues of the groups with an anti-KO antibody in the third week in the same way whether the transplanted TSCs remained. Finally, the survival curves of the groups were compared.

Suicide Gene Cell Therapy for Malignant Brain Tumor Using Therapeutic Stem Cells, TSCs (1) Expressing yCD-UPRT (Transplantation Model after Tumor Formation)

First, $1\times10^4$ cells/2 μl U87-ffLuc was transplanted to the right striate body (2 mm away from the anterior fontanel to the right and 3 mm deep from the brain surface) of each T cell-deficient mouse (female BALB/c nude mouse, 20 g, 6 w) subjected to general anesthesia, and $1\times10^6$ cells/2 μl TSCs expressing yCD-UPRT (yCD-UPRT is introduced into NS/PCs with the lentiviral vector) were stereotactically transplanted to the same site 5 days later. The take of tumor cells was confirmed 2 days later with an IVIS, that is, an in vivo imaging system, and 500 μl of 5-FC (10 mg/ml) was then intraperitoneally administered to a treated group once per day for 2 weeks (TSC (+)/5-FC (+) 5 mg/day, n=9). Next, 500 μl of 1 M PBS was administered to a control group 1 for 2 weeks in the same way (control group 1: TSC (+)/5-FC (−), n=9). A group to which only U87-ffLuc was transplanted was also generated as another control group, and 500 μl of 5-FC (10 mg/ml) was intraperitoneally administered to this once per day for 2 weeks (control group 2: TSC (−)/5-FC (+) 5 mg/day, n=3).

A method for evaluating tumors, the analysis of survival curves and the like were all performed in the same way as in the examination of the therapeutic effect of the above-mentioned mixture transplantation model.

Visualization of Bystander Effect and Migration of NS/PCs by Slice Culture Using Therapeutic Stem Cells, TSCs (2) Expressing yCD-UPRT (Time-Lapse Imaging)

First, $1\times10^5$ U87-ffLuc cells were stereotactically transplanted to the right striate body (2 mm away from the anterior fontanel to the right and 3 mm deep from the brain surface) of a T cell-deficient mouse (female BALB/c nude mouse, 20 g, 6 w) subjected to general anesthesia (Day 0). TSCs expressing yCD-UPRT (yCD-UPRT is introduced into NS/PCs with the lentiviral vector) were stereotactically transplanted to the same site on Day 7. The mouse was decapitated under non-perfusion, and brain sections having a thickness of 200 μm were prepared using a vibratome on the next day (Day 8). Slice culture was started on sterile porous (0.4 μm) insert membranes (Merck KGaA). Each glass bottom dish was filled with 1800 μl of NS (neurosphere) medium (to D-MEM/Ham's F-12 medium (containing HEPES) (produced by Wako Pure Chemical Industries, Ltd.) were added a 20 ng/ml recombination human epidermal growth factor (produced by PeproTech, Inc.), a 20 ng/ml recombination human fibroblast growth factor-2 (produced by PeproTech, Inc.), a 103 units/ml recombination human leukemia inhibitory factor (produced by NACALAI TESQUE, INC.), a 2% B-27 supplement (produced by Thermo Fisher Scientific K.K.) and 1 unit/ml heparin sodium (produced by AY PHARMACEUTICALS CO., LTD.)). The tumor was labeled with Venus in green, and TSCs were labeled with hKO1 in red. Time-lapse photography was performed through a confocal microscope for 5 days from the same day. In a treatment dish, 200 μl of 10 mg/ml 5-FC was administered to the above-mentioned medium. In a control dish 1, 200 μl of 1 M PBS was administered to the medium. As a control dish 2, 250 μM temozolomide was administered. The medium was replaced once every 2 days, and 5-FC, PBS and temozolomide were administered in the same way.

Suicide Gene Cell Therapy for Malignant Brain Tumor Using Therapeutic Stem Cells, TSCs (2) Expressing yCD-UPRT (Transplantation Model after Tumor Formation)

First, $1\times10^4$ cells/2 μl U87-ffLuc was transplanted to the right striate body (2 mm away from the anterior fontanel to the right and 3 mm deep from the brain surface) of each T cell-deficient mouse (female BALB/c nude mouse, 20 g, 6 w) subjected to general anesthesia, and $1\times10^6$ cells/2 μl TSCs expressing yCD-UPRT (yCD-UPRT is introduced into iPS cells with CRISPR/Cas9) were stereotactically transplanted to the same site 5 days later. The take of tumor cells was confirmed 2 days later with an IVIS, that is, an in vivo imaging system, and further 2 days later, 500 μl of 5-FC (10 mg/ml) was intraperitoneally administered to a treated group once per day for 2 weeks (TSC (+)/5-FC (+), n=8). Then, 500 μl of 1 M PBS was administered to a control group 1 for 2 weeks in the same way (control group 1: TSC/5-FC (−), n=7). A group to which only U87-ffLuc was transplanted was also generated as another control group, and 500 μl of 5-FC (10 mg/ml) was intraperitoneally administered to this once per day for 2 weeks (control group 2: TSC (−)/5-FC (+), n=3).

A method for evaluating tumors, the analysis of survival curves and the like were all performed in the same way as the above.

<Introduction of Tetracycline (Tet)-Induced yCD-UPRT Gene into iPS Cells Using Lentiviral Vector-Therapeutic Stem Cells, TSCs (3)>

Preparation of Lentiviral Vector Expressing Tet-Induced yCD-UPRT

The yCD-UPRT cDNA was subcloned into the lentiviral vector plasmid CSIV-RfA-TRE-EF-KT to obtain CSIV-yCD-UPRT-TRE-EF-KT. CSIV-yCD-UPRT-TRE-EF-KT was used for preparing a lentiviral vector expressing hKO1 and rtTA (reverse Tet-controlled transactivator) under the EF-1α promoter and expressing yCD-UPRT under the tetracycline (Tet)-induced promoter. The lentiviral vector was prepared by a known method.

Preparation of Tet-Induced NS/PCs Expressing yCD-UPRT

Human iPS cells were infected with the CSIV-yCD-UPRT-TRE-EF-KT lentiviral vector at an MOI of around 15 and cultured, the clones were then sorted with a cell sorter to obtain an iPS cell line expressing hKO1 steadily and highly. It was confirmed that the cell death of the Tet-induced iPS cells expressing yCD-UPRT was induced by adding 1 μg/ml doxycycline (Dox) and 1 μg/ml 5-FC to the medium.

Differentiation induction from the Tet-induced iPS cells expressing yCD-UPRT to NS/PCs was performed to obtain secondary and tertiary Tet-induced NS/PCs expressing yCD-UPRT. It was confirmed that the cell death of the Tet-induced NS/PCs expressing yCD-UPRT was also induced by adding 1 μg/ml Dox and 1 μg/ml 5-FC to the medium.

Suicide Gene Cell Therapy for Malignant Brain Tumor Using Tet-Induced Therapeutic Stem Cells, TSCs (3) Expressing yCD-UPRT (Mixture Transplantation Model)

First, $1\times10^5$ cells/2 μl U87-ffLuc and $5\times10^5$ cells/2 μl TSCs (3) (Tet-induced yCD-UPRT was introduced into iPS cells with the lentiviral vector) were mixed and stereotactically transplanted to the right striate body (2 mm away from the anterior fontanel to the right and 3 mm deep from the brain surface) of each T cell-deficient mouse (female BALB/c nude mouse, 20 g, 6 w) subjected to general anesthesia. Then, 500 μl of 5-FC (10 mg/ml) was intraperitoneally administered once per day for 2 weeks from the next day (treated group 1: TSC (+)/5-FC (+)/Dox (+), n=7). Next, 500 μl of 1 M PBS was administered to a control group 1 for 2 weeks in the same way (control group 1: TSC (+)/5-FC (+)/Dox (−), n=9). A group to which only U87-ffLuc was transplanted was also generated as another control group, and 500 μl of 5-FC (10 mg/ml) was intraperitoneally administered to this once per day for 2 weeks (control group 2: TSC (−)/5-FC (+)/Dox (+), n=4). Feed containing 200 mg/kg of Dox was orally ingested. A method for evaluating tumors, the analysis of survival curves and the like were all performed in the same way as the above.

(B) Results (1) Suicide Gene Cell Therapy for Malignant Brain Tumor Using Therapeutic Stem Cells (TSCs) Expressing yCD-UPRT (Mixture Transplantation Model)

<Summary>

FIG. 1 shows the summary of a suicide gene cell therapy when a mixture of therapeutic stem cells and tumor cells are transplanted (mixture transplantation model). Yeast cytosine deaminase (yCD) which was a suicide gene to be introduced and 5-fluorocytosine (5-FC) which was a prodrug were used in combination. Although CD suppresses DNA and RNA synthesis and induces cell death by converting 5-FC to 5-fluorouracil (5-FU), uracil phosphoribosyltransferase (UPRT) converts 5-FU to 5-FUMP, which is a thymidylate synthetase inhibitor, by combining yCD and the UPRT gene. Therefore, 100 times or more stronger bystander effect is obtained than that of yCD alone. A local bystander effect is dependent on the cell cycle, and only tumor cells are killed selectively. Therefore, a high therapeutic index is expected.

Induced Pluripotent Stem (iPS) cells were differentiation-induced into NS/PCs, and the yCD-UPRT gene was introduced with the lentiviral vector to establish therapeutic stem cells (TSCs) expressing the suicide gene yCD-UPRT.

A mixture of $1\times10^5$ human glioma cells (U87) and $5\times10^5$ TSCs was transplanted to the T cell-deficient mouse brain (right striate body). In a treated group 1 (Group 1), 250 mg/kg of 5-fluorocytosine (5-FC) was administered once per day for 21 days from the day following the transplantation (TSC (+)/5FC (+) 5 mg/day, n=9). In a treated group 2 (Group 2), the dose was reduced, and 50 mg/kg was administered in the same way (TSC (+)/5FC 1 mg/day, n=9). PBS was administered to a control group 1 (Group 3) (TSC (+)/5FC (−), n=9). In a control group 2 (Group 4), only $1\times10^5$ U87 cells were transplanted in the same way, and 250 mg/kg of 5-FC was administered for the same period (TSC (−)/5FC (+) 5 mg/day, n=3).

The survival analysis was performed while the luminescence imaging analysis (IVIS) of tumors was performed chronologically. Some mice were euthanized in the third week after the transplantation, and the histological analysis of the brains was performed.

<Chronological Analysis of Tumors by Luminescence Imaging Analysis (IVIS)>

Figure 2:
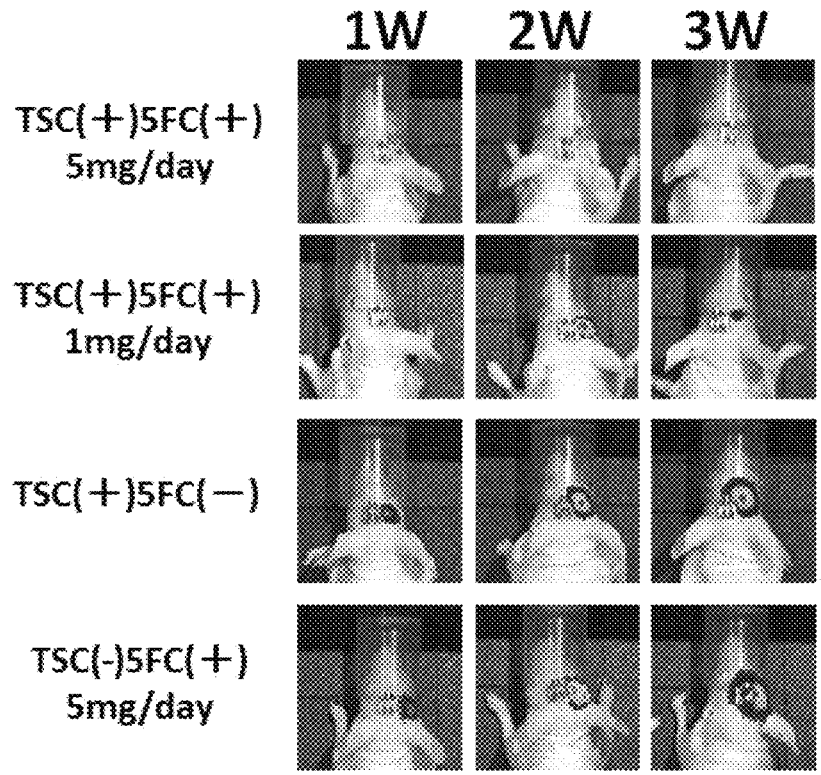
FIG. 2 shows the results of the luminescence imaging analysis (IVIS) of tumors.
Figure 3:
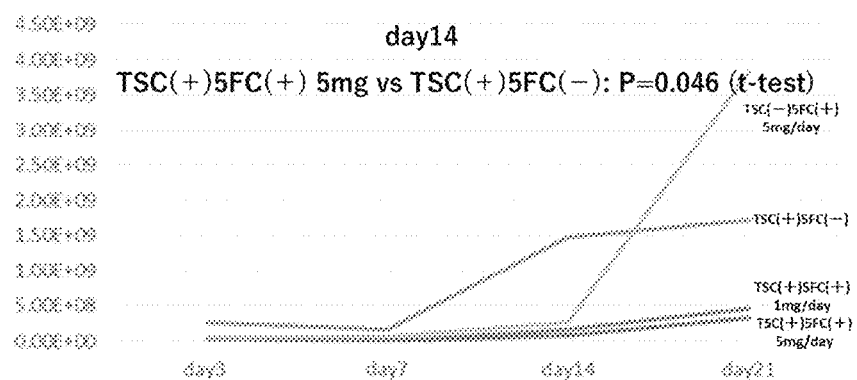
FIG. 3 shows the measurement results of the ROI values of the luminescence imaging.

Tumors tended to be smaller in both treated groups than in both control groups (FIG. 2). When the ROI values of the luminescence imaging were measured, the ROI values of the treated group were significantly low, and the ROI values were remarkably low especially from the second week onward (FIG. 3) (TSC (+)/5FC (+) 5 mg/day vs TSC (+)/5FC (−), the second week, P=0.0046, t-test).

<Histological Analysis of Brain Tumor Model Mice (in the Third Week after the Transplantation of Glioma Cells and TSCs: n=3)>

Figure 4:
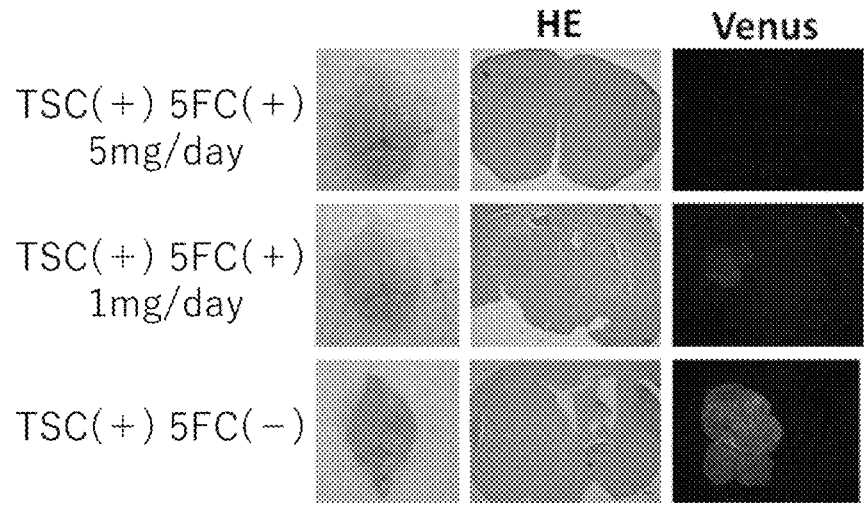
FIG. 4 shows photographs of brains extracted from mice (left), HE-stained images of mouse brain sections (center) and Venus fluorescence images of mouse brain sections (right).
Figure 5:
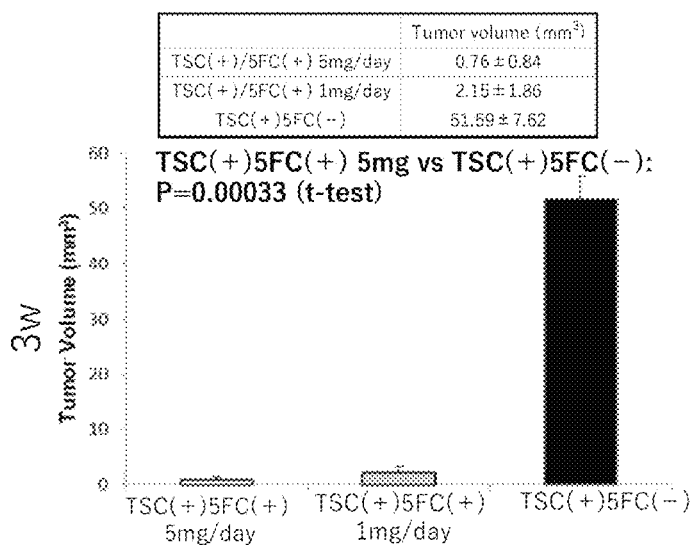
FIG. 5 shows the results of the analysis of tumor volumes.

Since the fluorescence protein Venus gene was introduced into the glioma cells (U87), the tumor volumes were quantitatively analyzed using a fluorescence microscope. The tumor volume of the treated group 1 was 0.76±0.84 mm$^3$, and the tumor volume of the treated group 2 was 2.15±1.86 mm$^3$. Both were significantly small as compared with 51.59±7.62 mm$^3$ of the control group 1 (FIG. 4 and FIG. 5) (TSC (+)/5FC (+) 5 mg/day vs TSC (+)/5FC (−), P=0.00033, t-test). The tumor volume of the treated group 1 tended to be still smaller than that of the treated group 2. Moreover, in the treated group 1, the tumor of one of the three mice was not confirmed in the third week, and the result was that complete disappearance of the tumor was expected.

Figure 6:
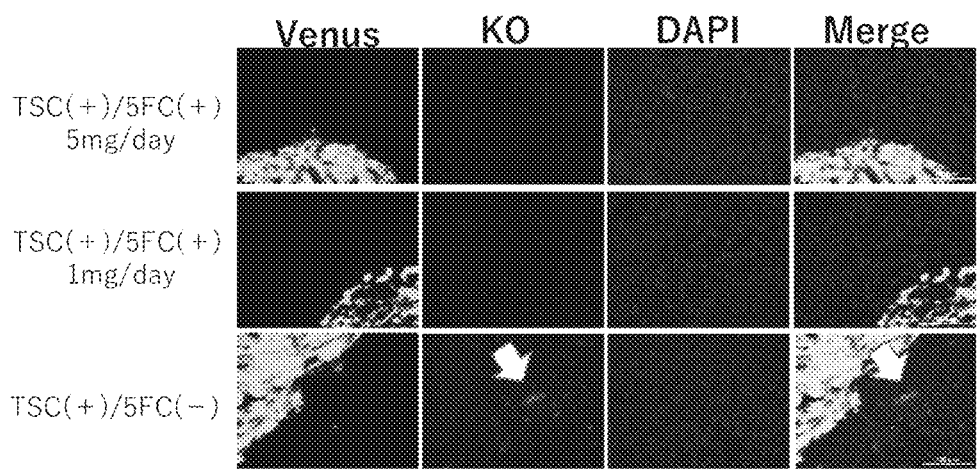
FIG. 6 shows the results of the survival analysis of the transplanted TSCs. The upper row and the middle row show treated groups, and the lower row shows a control group. From the left, images stained with Venus (U87 tumor cells are stained), images stained with KO (TSCs are stained), images stained with DAPI (nuclei are stained), and a merge (fused image of Venus, KO and DAPI).

The extinction of the above-mentioned transplanted TSCs in the mouse brains was confirmed as to the safety of the present therapy (the risk of the tumorigenesis of iPS cells). Since the Kusabira-Orange (KO) gene was introduced into the TSCs, the TSCs were analyzed by fluorescence staining using a KO antibody. Consequently, although the transplanted TSCs remained in the brains in the control group, clear survival of the transplanted TSCs was not observed in both treated groups (n=3 in each group) (FIG. 6). It was therefore confirmed that the transplanted TSCs died within three weeks by the yCD-UPRT/5FC system.

<Survival Analysis of Brain Tumor Model>

Figure 7:
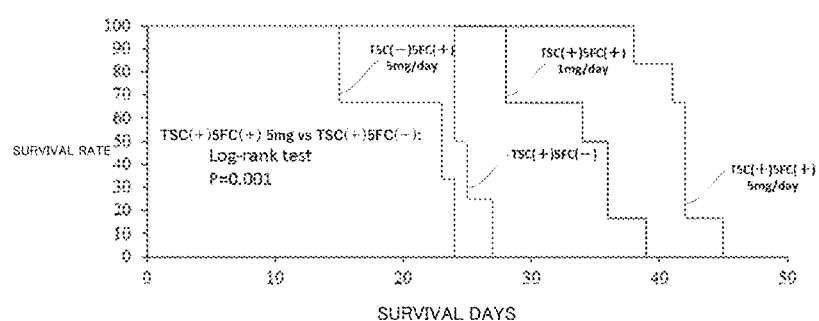
FIG. 7 shows the results of the survival analysis of brain tumor models.

In both treated groups, significant extension of the survival periods was observed as compared with both control groups (FIG. 7). The average survival period of the treated group 1 was 42 days, the average survival period of the treated group 2 was 34 days, the average survival period of the control group 1 was 25 days, and the average survival period of the control group 2 was 21 days (TSC (+)/5FC (+) 5 mg/day vs TSC (+)/5FC (−), logrank, p=0.001). The survival period of the treated group 1 was significantly still longer than that of the treated group 2.

(2) Suicide Gene Cell Therapy for Malignant Brain Tumors Using Therapeutic Stem Cells (TSCs) Expressing yCD-UPRT (Transplantation Model after Tumor Formation).

Summary

Figure 8:
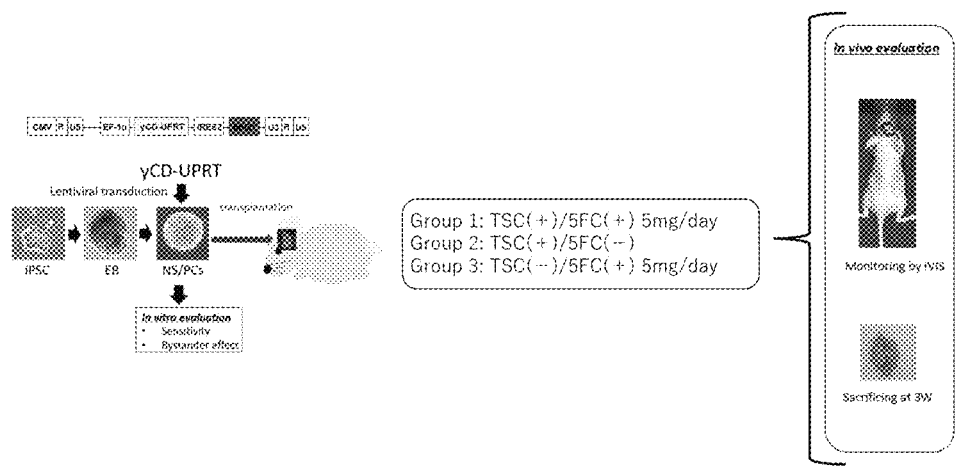
FIG. 8 shows the summary of a suicide gene cell therapy for malignant brain tumors using therapeutic stem cells (TSCs) expressing yCD-UPRT (transplantation model after tumor formation).

FIG. 8 shows the summary of a suicide gene cell therapy when therapeutic stem cells are transplanted after tumor formation (transplantation model after tumor formation). Induced Pluripotent Stem (iPS) cells were differentiation-induced into NS/PCs, and the yCD-UPRT gene was then introduced with the lentiviral vector in the same way as in the mixture transplantation model to establish therapeutic stem cells (TSCs) expressing the suicide gene yCD-UPRT.

First, 1×10$^4$ human glioma cells (U87) were transplanted to the T cell-deficient mouse brain (right striate body), and 1×10$^6$ TSCs were stereotactically transplanted to the same site 5 days later. The take of tumor cells was confirmed 4 days later with an IVIS, that is, an in vivo imaging system, 5-FC (250 mg/kg) was then intraperitoneally administered to a treated group (Group 1) once per day for 2 weeks (TSC (+)/5FC (+) 5 mg/day, n=9). PBS was administered to a control group 1 (Group 2) for 2 weeks in the same way (TSC (+)/5FC (−), n=9). Only U87 was transplanted in a control group 2 (Group 3), and 5-FC (250 mg/kg) was administered once per day for 2 weeks (TSC (−)/5FC (+) 5 mg/day, n=3).

The survival analysis was performed while the luminescence imaging analysis (IVIS) of tumors was performed chronologically. Some mice were euthanized in the third week after the tumor transplantation, and the histological analysis of the brains was performed.

<Chronological Analysis of Tumors by Luminescence Imaging Analysis (IVIS)>

Figure 9:
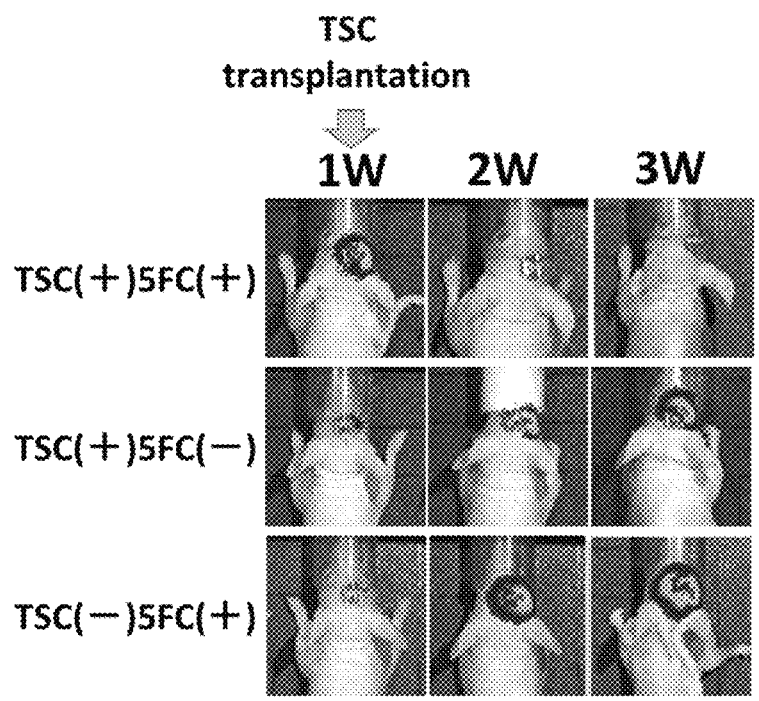
FIG. 9 shows the results of the luminescence imaging analysis (IVIS) of tumors.
Figure 10:
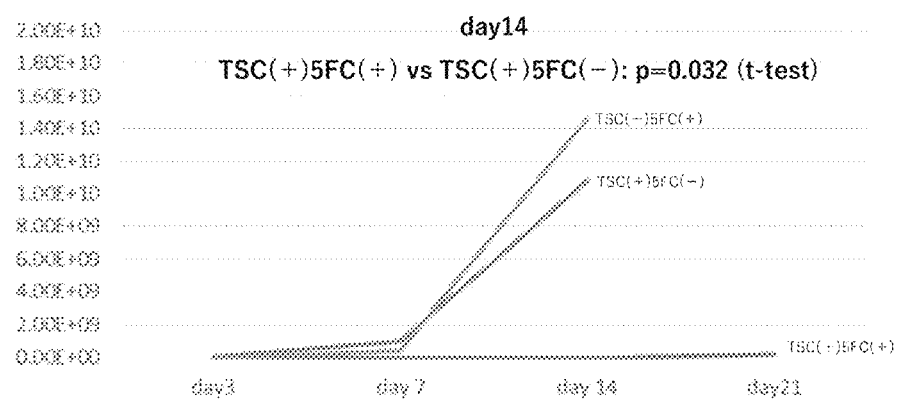
FIG. 10 shows the measurement results of the ROI values of the luminescence imaging.

A tumor tended to be smaller in the treated group than in both control groups (FIG. 9). When the ROI values of the luminescence imaging were measured, the ROI values of the treated group were significantly low, and the ROI values were remarkably low especially from the second week onward (FIG. 10) (TSC (+)/5FC (+) vs TSC (+)/5FC (−), P=0.032, t-test).

<Histological Analysis of Brain Tumor Model Mice (in the Third Week after the Transplantation of Glioma Cells and TSCs: n=3)>

Figure 11:
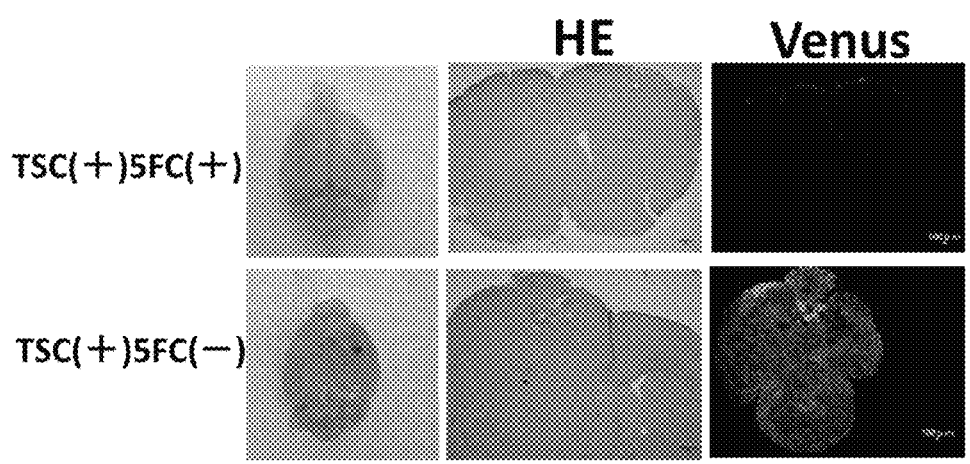
FIG. 11 shows photographs of brains extracted from mice (left), HE-stained images of mouse brain sections (center) and Venus fluorescence images of mouse brain sections (right).
Figure 12:
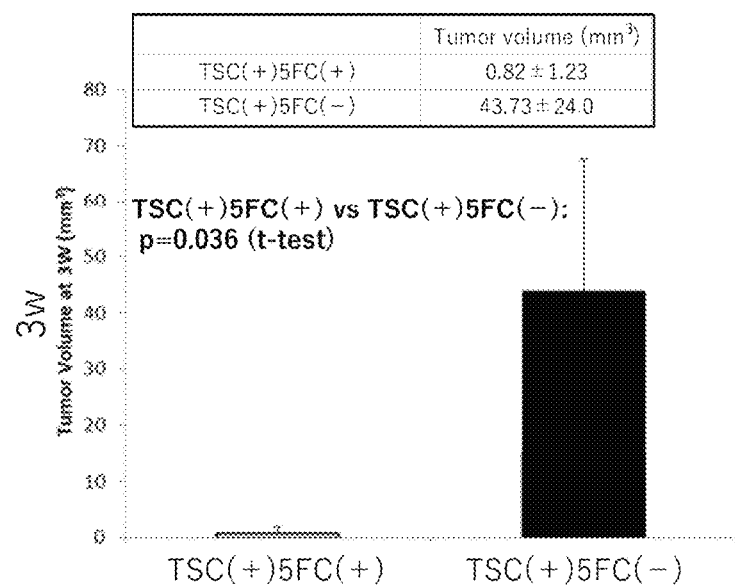
FIG. 12 shows the results of the analysis of tumor volumes.

Since the fluorescence protein Venus gene was introduced into the glioma cells (U87), the tumor volumes were quantitatively analyzed using a fluorescence microscope. The tumor volume of the treated group was 0.82±1.23 mm$^3$, and was significantly small as compared with 43.73±24.0 mm$^3$ of the control group 1 (FIGS. 11 and 12) (TSC (+)/5FC (+) vs TSC (+)/5FC (−), P=0.036, t-test).

Figure 13:
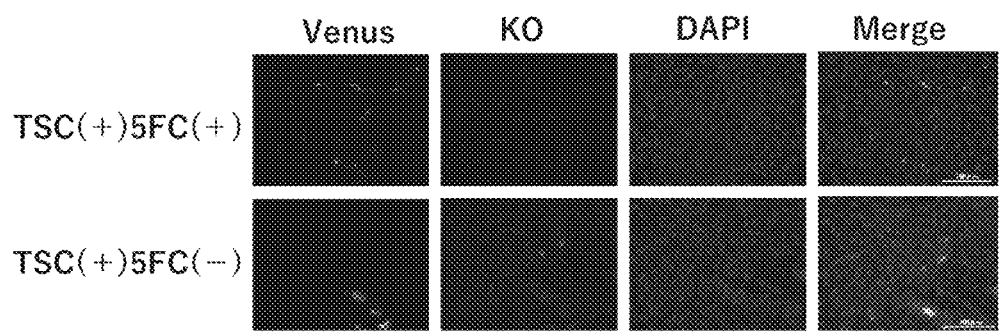
FIG. 13 shows the results of the survival analysis of transplanted TSCs. The upper row shows a treated group, and the lower row shows a control group. From the left, images stained with Venus (U87 tumor cells are stained), images stained with KO (TSCs are stained), images stained with DAPI (nuclei are stained), and a merge (fused image of Venus, KO and DAPI).

The extinction of the above-mentioned transplanted TSCs in the mouse brains was confirmed as to the safety of the present therapy (the risk of the tumorigenesis of iPS cells). Since the Kusabira-Orange (KO) gene was introduced into the TSCs, the TSCs were analyzed by fluorescence staining using a KO antibody. Consequently, although the transplanted TSCs remained in the brains in the control group 1, clear survival of the transplanted TSCs was not observed in the treated group (n=3 in each group) (FIG. 13). It was therefore confirmed that the transplanted TSCs died within three weeks by the yCD-UPRT/5FC system.

<Survival Analysis of Brain Tumor Model>

Figure 14:
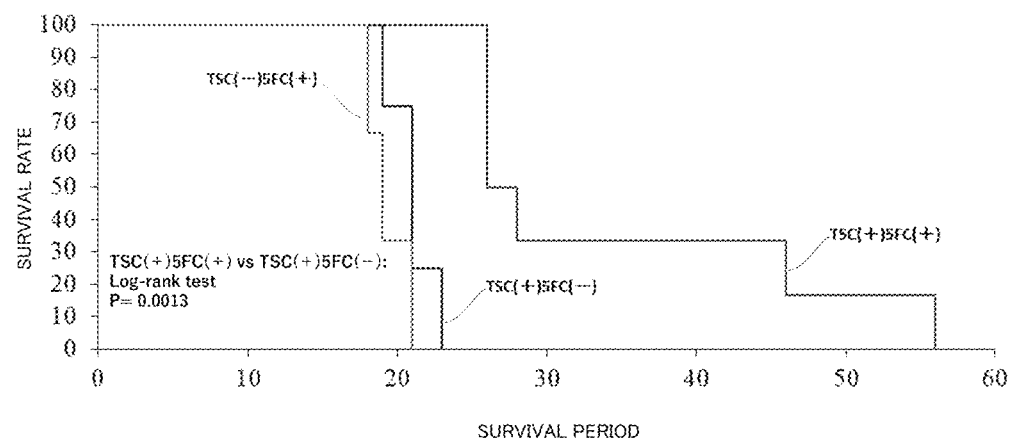
FIG. 14 shows the results of the survival analysis of brain tumor models.

In the treated group, significant extension of the survival periods was observed as compared with both control groups (FIG. 14). The average survival period of the treated group was 36 days, the average survival period of the control group 1 was 20 days, and the average survival period of the control group 2 was 21 days (TSC (+)/5FC (+) vs TSC (+)/5FC (−), logrank, p=0.0013).

As mentioned above, when yCD-UPRT was introduced into NS/PCs derived from human iPS cells using a lentiviral vector which can be applied clinically, and the NS/PCs were transplanted to a human brain tumor model mouse, a remarkable therapeutic effect (bystander effect) was observed by administering 5-FC, and the efficacy of the present therapy could be proved.

<Time-Lapse Imaging by Method for Brain Slice Culture>

Figure 15:
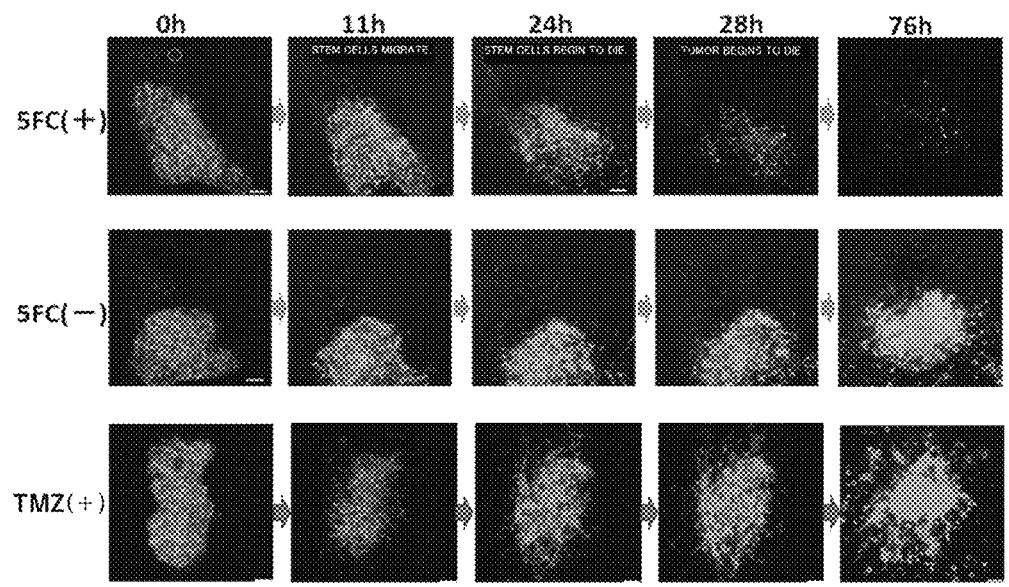
FIG. 15 shows the results of time-lapse imaging of TSCs expressing yCD-UPRT. The upper row shows a treated group, the middle row shows a control group 1, and the lower row shows a control group 2.
Figure 16:
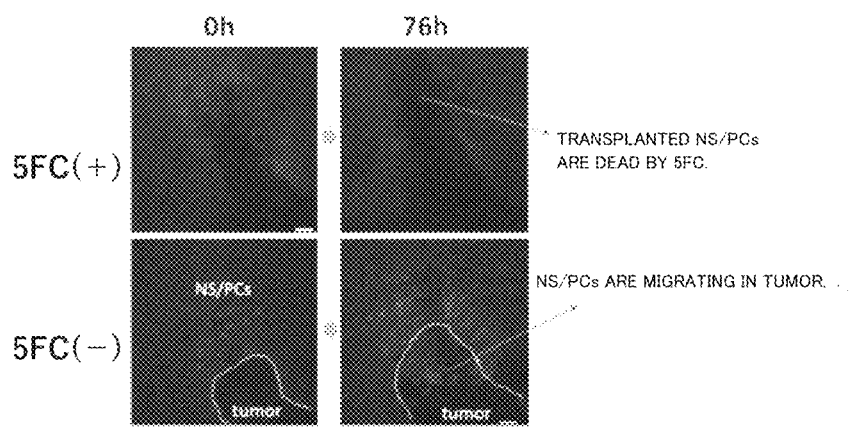
FIG. 16 shows KO-stained images of TSCs expressing yCD-UPRT. The upper row shows a treated group and the lower row shows a control group 1.
Figure 17:
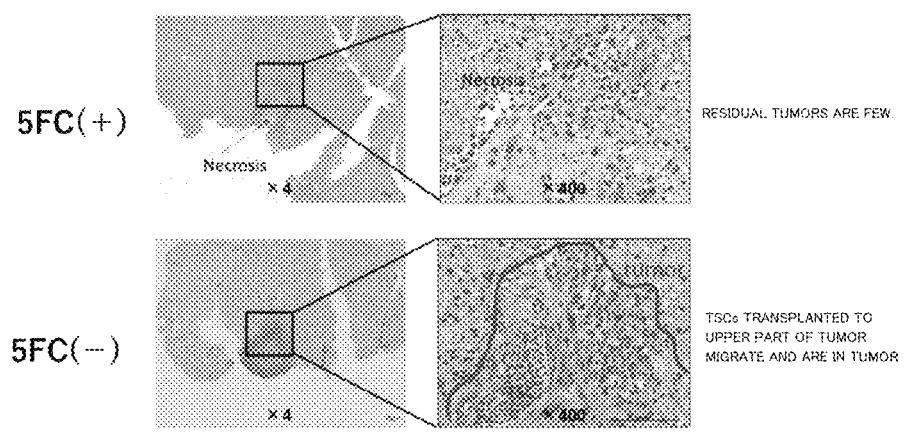
FIG. 17 shows HE-stained images of TSCs expressing yCD-UPRT. The upper row shows a treated group and the lower row shows a control group 1.

First, 1×10$^5$ ffLuc-U87 cells were stereotactically transplanted to a T cell-deficient mouse (right striate body) (Day 0). TSCs (TSCs prepared by differentiation-inducing iPS cells into NS/PCs, and then introducing the yCD-UPRT gene into the NS/PCs with the lentiviral vector) were stereotactically transplanted to the same site on Day 7. The mouse was decapitated under non-perfusion, and brain sections having a thickness of 200 μm were prepared using a vibratome on the next day. Slice culture was started on sterile porous (0.4 μm) insert membranes. The tumor was labeled with Venus in green, and TSCs were labeled with hKO1 in red. Photography was performed through a confocal microscope for 5 days from the same day. As a treated group, 200 µl of 10 mg/ml 5-FC was administered to the medium. As a control group 1, 200 µl of 1 M PBS was administered to the medium. As a control group 2, 250 µM temozolomide was administered. It could be observed that, in the treated group, the transplanted TSCs migrated, diffused in a tumor, then satisfactorily reacted to 5-FC and died, and surrounding tumors then died (FIG. 15, FIG. 16 and FIG. 17). It could be confirmed that, in the control group 1, TSCs continued surviving, migrated and entered the tumor (FIG. 15, FIG. 16 and FIG. 17). As the control group 2, although temozolomide had the effect of suppressing temporary tumor increase, it was not observed that temozolomide had the effect of reducing the tumor (FIG. 15).

(3) Suicide Gene Cell Therapy for Malignant Brain Tumors Using Therapeutic Stem Cells (TSCs) Expressing yCD-UPRT with CRISPR/Cas9 (Transplantation Model after Tumor Formation)

<Summary>

Figure 18:
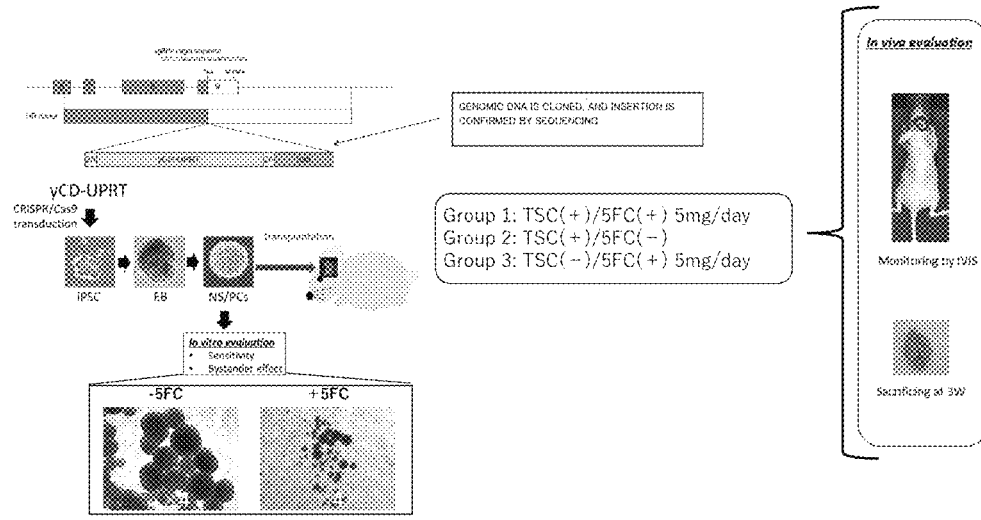
FIG. 18 shows the summary of a suicide gene cell therapy for malignant brain tumors using therapeutic stem cells (TSCs) expressing yCD-UPRT with CRISPR/Cas9 (transplantation model after tumor formation).

FIG. 18 shows the summary of a suicide gene cell therapy using iPS cells into which the suicide gene is incorporated by genome editing. It is desirable to introduce the yCD-UPRT gene into human iPS cells for steady supply of therapeutic neural stem cells. Since the gene is inserted into chromosomes at random in gene introduction with the lentiviral vector, the gene variations of the insertion sites, the activation of peripheral genes and the inactivation of yCD-UPRT by positional effect are concerned. iPS cells in which yCD-UPRT was inserted into the GAPDH gene region were prepared using CRISPR/Cas9 genome editing techniques to solve this problem. NS/PCs were induced from these iPS cells to obtain therapeutic stem cells (TSCs) expressing yCD-UPRT.

First, $1\times10^4$ human glioma cells (U87) were transplanted to the T cell-deficient mouse brain (right striate body), and $1\times10^6$ TSCs were stereotactically transplanted to the same site 5 days later. The take of tumor cells was confirmed 4 days later with an IVIS, that is, an in vivo imaging system, 5-FC (250 mg/kg) was then administered to a treated group (Group 1) once per day (TSC (+)/5FC (+), n=6). PBS was administered to a control group 1 (Group 2) for 2 weeks in the same way (TSC/5FC (−), n=4). Only U87 was transplanted in a control group 2 (Group 3), and 5-FC (250 mg/kg) was intraperitoneally administered once per day for 2 weeks (TSC (−)/5FC (+), n=3).

The survival analysis was performed while the luminescence imaging analysis (IVIS) of tumors was performed chronologically. Some mice were euthanized in the third week after the tumor transplantation, and the histological analysis of the brains was performed.

<Chronological Analysis of Tumors by Luminescence Imaging Analysis (IVIS)>

Figure 19:
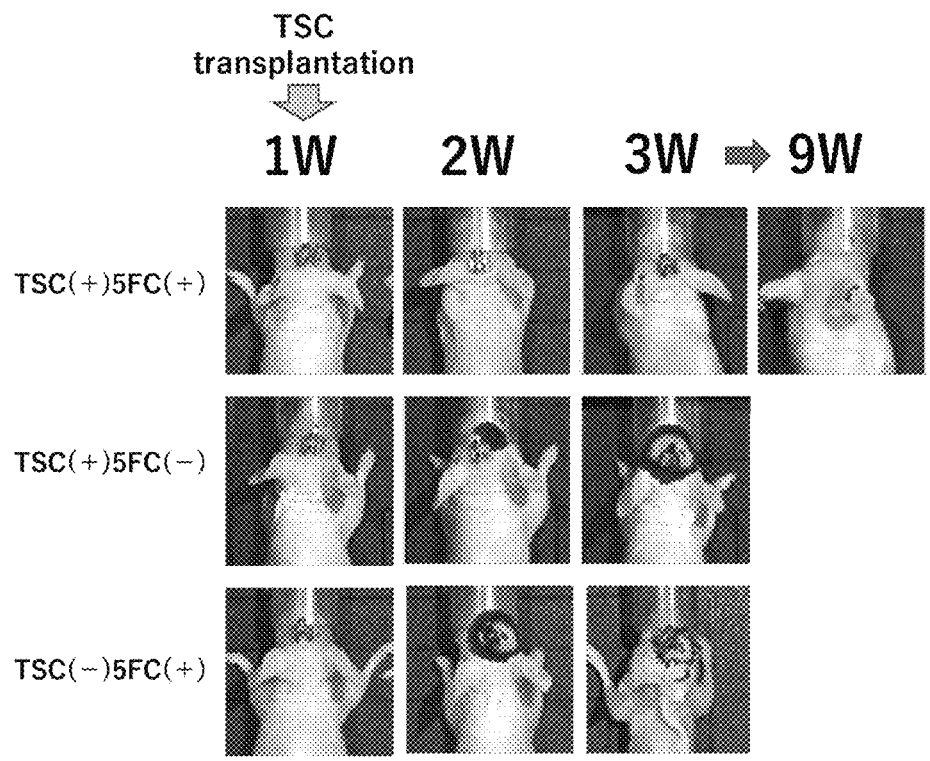
FIG. 19 shows the results of the luminescence imaging analysis (IVIS) of tumors.
Figure 20:
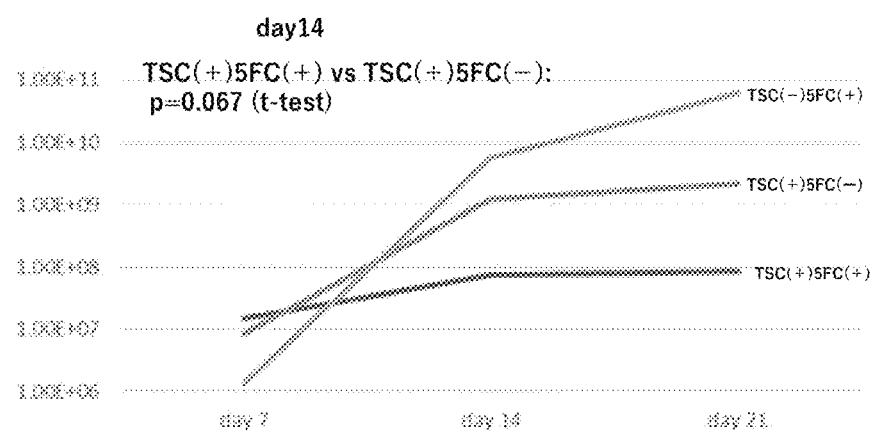
FIG. 20 shows the measurement results of the ROI values of the luminescence imaging.

A tumor tended to be smaller in the treated group than in both control groups (FIG. 19). When the ROI values of the luminescence imaging were measured, the ROI values of the treated group tended to be low, and the ROI values were remarkably low especially from the second week onward (FIG. 20) (TSC (+)/5FC (+) vs TSC (+)/5FC (−), P=0.067, t-test).

<Histological Analysis of Brain Tumor Model Mice (in the Third Week after Transplantation of Glioma Cells and TSCs: n=3)>

Figure 21:
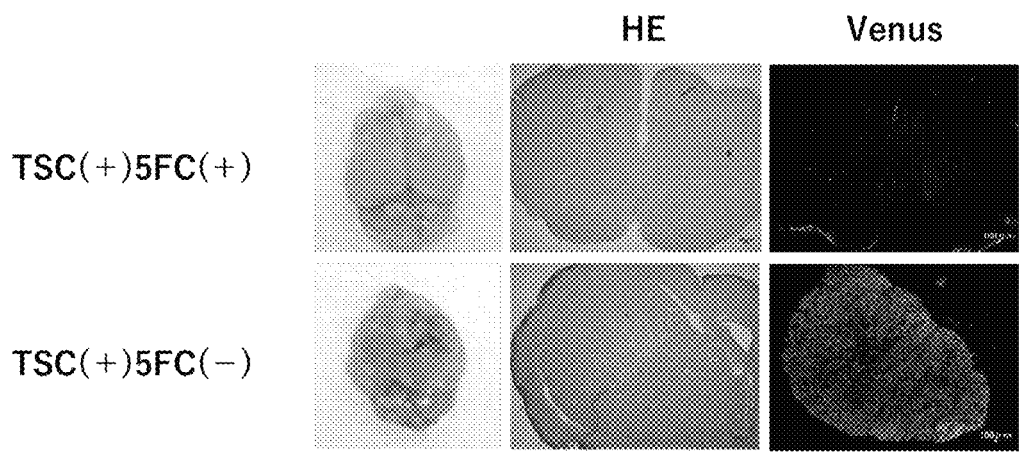
FIG. 21 shows photographs of brains extracted from mice (left), HE-stained images of mouse brain sections (center) and Venus fluorescence images of mouse brain sections (right).
Figure 22:
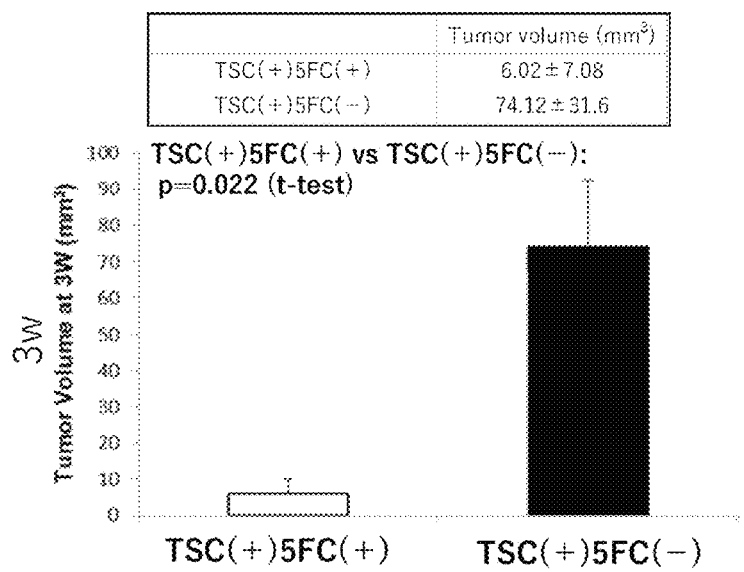
FIG. 22 shows the results of the analysis of tumor volumes.

Since the fluorescence protein Venus gene was introduced into the glioma cells (U87), the tumor volumes were quantitatively analyzed using a fluorescence microscope. The tumor volume of the treated group was 6.02±7.08 mm³, and was significantly small as compared with 74.12±31.6 mm³ of the control group (FIG. 21 and FIG. 22) (TSC (+)/5FC (+) vs TSC (+)/5FC (−), P=0.022, t-test). In the treated group, an individual in which the tumor disappeared completely was also observed (the take of the tumor cells was confirmed with IVIS before 5-FC administration on Day 7).

<Survival Analysis of Brain Tumor Model>

Figure 23:
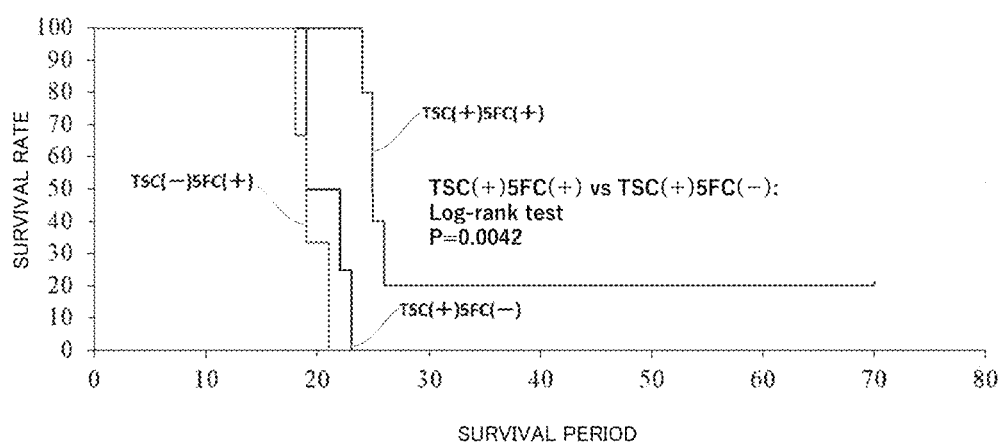
FIG. 23 shows the results of the survival analysis of brain tumor models.

In the treated group, significant extension of the survival period was observed as compared with both control groups (FIG. 23). The average survival period of the treated group was 35 days (one mouse in the group was finished for analysis), the average survival period of the control group 1 was 20 days, and the average survival period of the control group 2 was 21 days (TSC (+)/5FC (+) vs TSC (+)/5FC (−), logrank, p=0.0042). In the treated group, a case in which the tumor disappeared completely, and a mouse continued surviving was also observed.

(4) Suicide Gene Cell Therapy for Malignant Brain Tumors Using Tet-Induced Therapeutic Stem Cells, TSCs Expressing yCD-UPRT (Mixture Transplantation Model)

<Summary>

Figure 24:
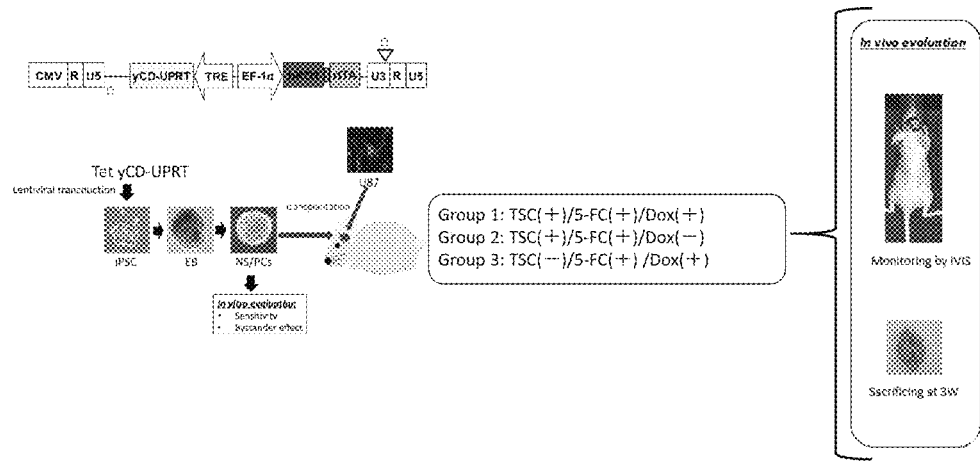
FIG. 24 shows the summary of a suicide gene cell therapy for malignant brain tumors using Tet-induced therapeutic stem cells, that is, TSCs, expressing yCD-UPRT (mixture transplantation model).

FIG. 24 shows the summary of a suicide gene cell therapy for malignant brain tumors using Tet-induced therapeutic stem cells, TSCs expressing yCD-UPRT. To introduce the yCD-UPRT gene into not NS/PCs but iPS cells with the lentiviral vector, yCD-UPRT which can be induced with tetracycline was introduced into the iPS cells with the lentiviral vector so that the gene was expressed only when doxycycline (Dox) was added. Consequently, the iPS cells could be induced into NS/PCs without problems through EBs with Dox not added, yCD-UPRT was then expressed by adding Dox, and NS/PCs which react to 5-FC satisfactorily were obtained thereby.

First, $1\times10^5$ cells/2 µl U87-ffLuc and $5\times10^5$ cells/2 µl TSCs were mixed and stereotactically transplanted to the right striate body (2 mm away from the anterior fontanel to the right and 3 mm deep from the brain surface) of each T cell-deficient mouse (female BALB/c nude mouse, 20 g, 6 w) subjected to general anesthesia. Then, 500 µl of 5-FC (10 mg/ml) was intraperitoneally administered once per day for 2 weeks from the next day (treated group (Group 1): TSC (+)/5-FC (+)/Dox (+), n=7). Next, 500 µl of 1 M PBS was administered to a control group 1 (Group 2) for 2 weeks in the same way (control group 1: TSC (+)/5-FC (+)/Dox (−), n=9). A group to which only U87-ffLuc was transplanted was also generated as another control group (Group 3), and 500 µl of 5-FC (10 mg/ml) was intraperitoneally administered to this once per day for 2 weeks (control group 2: TSC (−)/5-FC (+)/Dox (+), n=4). Feed containing 200 mg/kg of Dox was orally ingested. A method for evaluating tumors, the analysis of survival curves and the like were all performed in the same way as the above.

Survival analysis was performed, while the luminescence imaging analysis (IVIS) of the tumors was performed chronologically. Some mice were euthanized in the third week after the tumor transplantation, and the histological analysis of the brains was performed.

<Chronological Analysis of Tumors by Luminescence Imaging Analysis (IVIS) and Tumor Volume>

Figure 25:
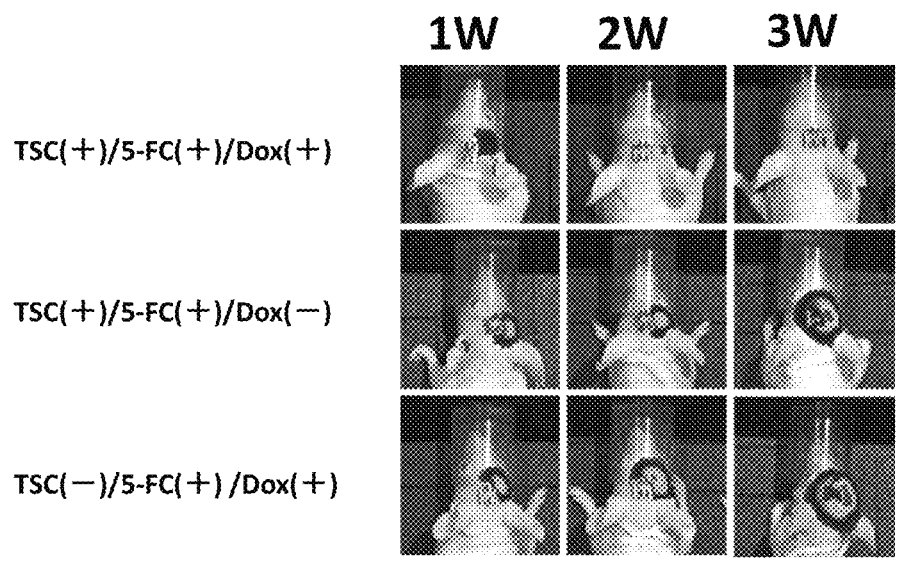
FIG. 25 shows the results of the luminescence imaging analysis (IVIS) of tumors.
Figure 26:
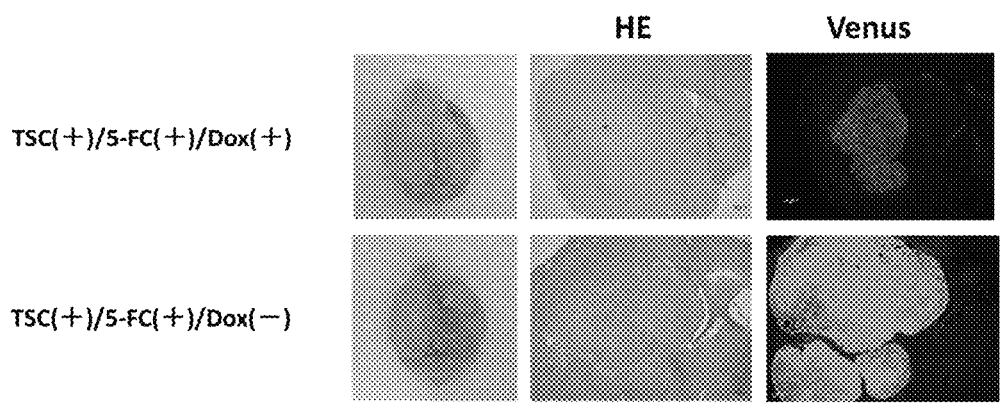
FIG. 26 shows photographs of brains extracted from mice (left), HE-stained images of mouse brain sections (center) and Venus fluorescence images of mouse brain sections (right).

A tumor tended to be smaller in the treated group than in both control groups (FIG. 25). Since the fluorescence protein Venus gene was introduced into the glioma cells (U87), the tumor volumes were quantitatively analyzed using a fluorescence microscope. The tumor volume of the treated group tended to be small as compared with the control group (FIG. 26).

<Survival Analysis of Brain Tumor Model>

Figure 27:
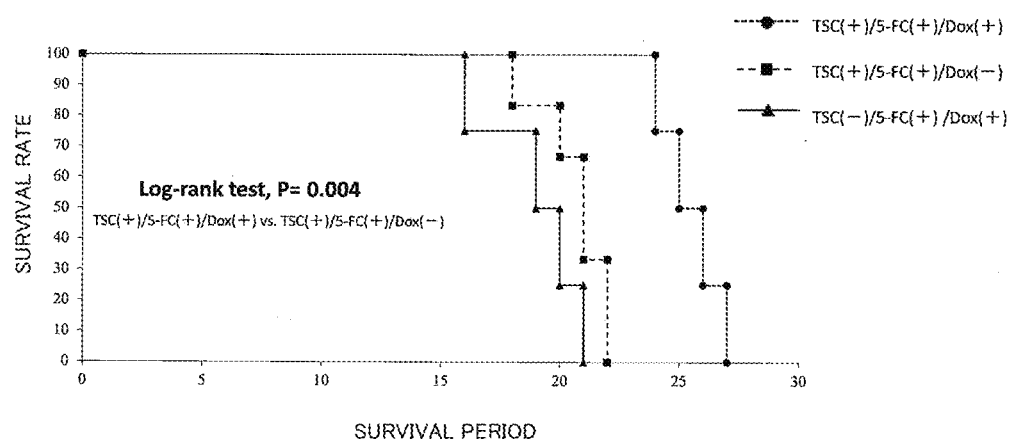
FIG. 27 shows the results of the survival analysis of brain tumor models.
Figure 28:
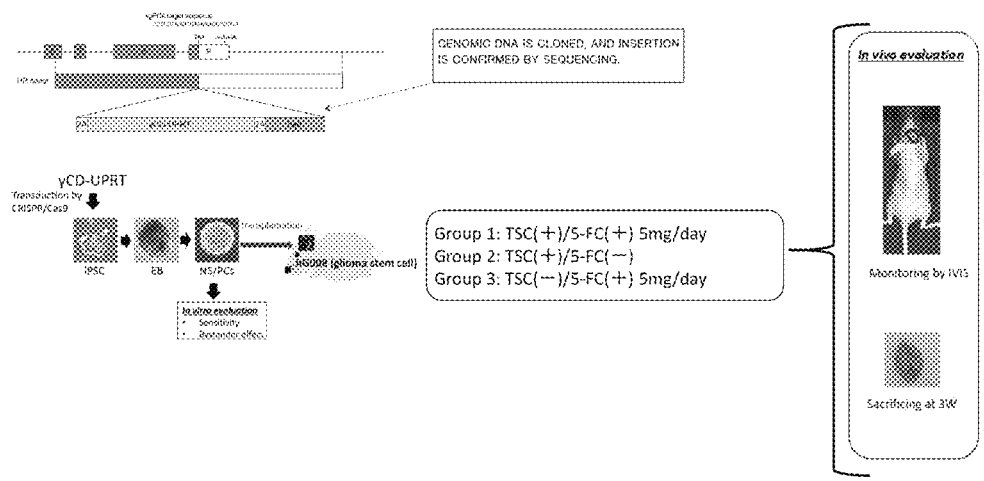
FIG. 28 shows the summary of a suicide gene cell therapy for malignant brain tumor stem cells using therapeutic stem cells (TSCs) expressing yCD-UPRT with CRISPR/Cas9 (transplantation model after tumor formation).

In the treated group, significant extension of the survival period was observed as compared with both control groups (FIG. 27). The average survival period of the treated group was 25.5 days, the average survival period of the control group 1 was 20 days, and the average survival period of the control group 2 was 19 days (TSC (+)/5-FC (+)/Dox (+) vs TSC (+)/5-FC (+)/Dox (−), logrank, p=0.004).

[Example 2] Suicide Gene Cell Therapy for Glioma Stem Cells

<Suicide Gene Cell Therapy for Malignant Brain Tumor Stem Cells (hG008) Using Therapeutic Stem Cells (TSCs) Expressing yCD-UPRT with CRISPR/Cas9 (Transplantation Model after Tumor Formation)>

First, a $5\times10^5$ cells/2 μl human glioma stem cell line hG008-ffLuc was transplanted to the right striate body (2 mm away from the anterior fontanel to the right and 3 mm deep from the brain surface) of each T cell-deficient mouse (female BALB/c nude mouse, 20 g, 6 w) subjected to general anesthesia, and $1\times10^6$ cells/2 μl TSCs expressing yCD-UPRT (yCD-UPRT is introduced into iPS cells with CRISPR/Cas9) were stereotactically transplanted to the same site 45 days later. The signal of the tumor was confirmed 7 days later with an IVIS, that is, an in vivo imaging system, and 500 μl of 5-FC (10 mg/ml) was then administered to a treated group once per day for 2 weeks (TSC (+)/5-FC (+) 5 mg/day, n=8). Next, 500 μl of 1 M PBS was administered to a control group 1 for 2 weeks in the same way (control group 1: TSC (+)/5-FC (−), n=7). A group to which only hG008-ffLuc was transplanted was also generated as another control group, and 500 μl of 5-FC (10 mg/ml) was intraperitoneally administered to this once per day for 2 weeks (control group 2: TSC (−)/5-FC (+) 5 mg/day, n=3).

A method for evaluating tumors, the analysis of survival curves and the like were all performed in the same way as in the examination of the therapeutic effect of the above-mentioned mixture transplantation model.

<Chronological Analysis of Tumors by Luminescence Imaging Analysis (IVIS)>

Figure 29:
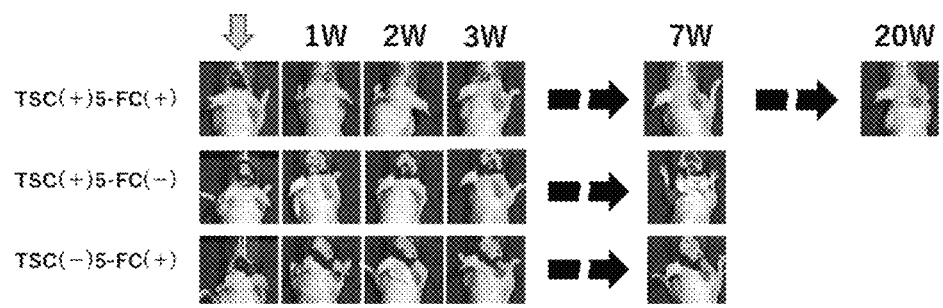
FIG. 29 shows the results of the luminescence imaging analysis (IVIS) of tumors.
Figure 30:
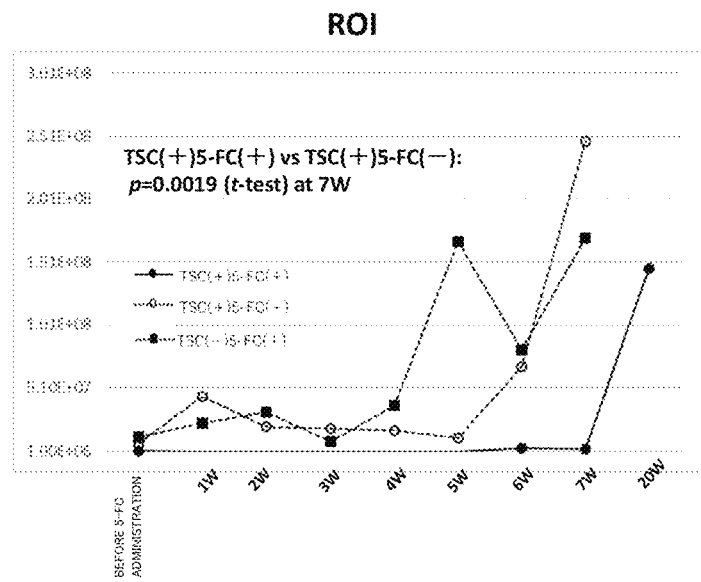
FIG. 30 shows the measurement results of the ROI values of the luminescence imaging.

In an IVIS, that is, an in vivo imaging system, the signal of the treated group decreased remarkably after 5-FC administration as compared with the two control groups (FIG. 29). The ROI of the signal of the IVIS of the treated group was significantly low, with p=0.0019 at the time of 7 W after 5-FC administration, which significantly demonstrated a significant difference between the treated group and the control group 1 (FIG. 30).

Figure 31:
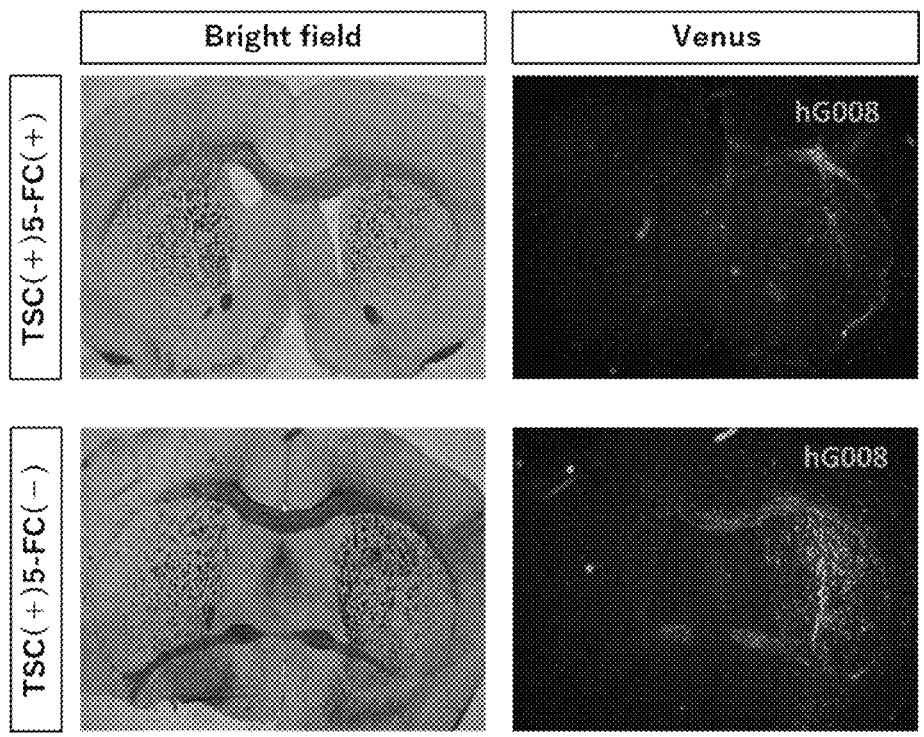
FIG. 31 shows the results of residual tumor analysis.
Figure 32:
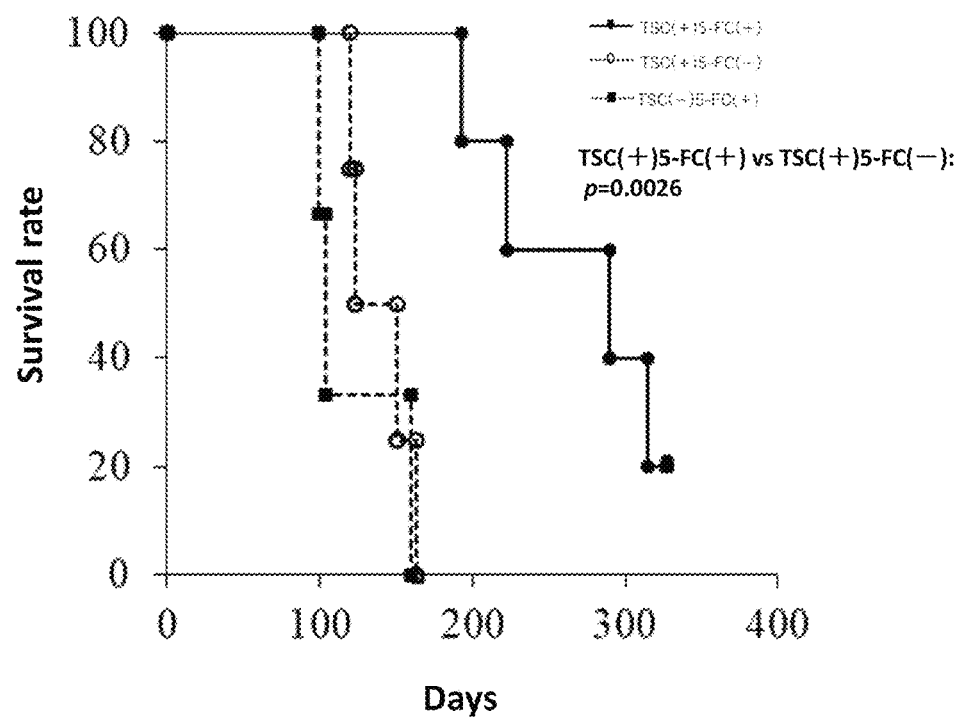
FIG. 32 shows the results of the survival analysis of brain tumor models.

<Histological Analysis of Brain Tumor Model Mouse> hG008 is fluorescently labeled with Venus fluorescence protein and visualized. Since the tumor model is a tumor model which infiltrates diffusely, the measurement of volume is difficult. However, the tumors of the treated group decrease clearly as compared with the control group 1 (FIG. 31). Tumors which infiltrate contralaterally are little observed in the treated group (FIG. 31).

<Survival Analysis of Brain Tumor Model>

The survival curve of the treated group was extended significantly, with p=0.0026 in the log-rank test, which demonstrated a significant difference between the treated group and the control group 1.

All of the publications, patents and patent applications cited herein are incorporated herein as reference as they are.

INDUSTRIAL APPLICABILITY

Since a cell preparation for treating brain tumors of the present invention can be used as a pharmaceutical, the present invention can be used in industrial fields such as medicine manufacture.

The invention claimed is:

1. A cell preparation for treating brain tumors used in combination with a prodrug that is converted to 5-fluorouracil by cytosine deaminase, wherein the cell preparation comprises neural stem cells derived from pluripotent stem cells having a cytosine deaminase gene and a uracil phosphoribosyltransferase gene.

2. The cell preparation for treating brain tumors according to claim 1, wherein the prodrug that is converted to 5-fluorouracil by cytosine deaminase is 5-fluorocytosine.

3. The cell preparation for treating brain tumors according to claim 1, wherein the neural stem cells derived from pluripotent stem cells are neural stem cells obtained by performing the following step (1) and then performing the following step (2):
(1) introducing a cytosine deaminase gene and a uracil phosphoribosyltransferase gene into pluripotent stem cells,
(2) differentiating the pluripotent stem cells into neural stem cells.

4. The cell preparation for treating brain tumors according to claim 3, wherein the cytosine deaminase gene and the uracil phosphoribosyltransferase gene are inserted into the genome of the pluripotent stem cells by genome editing.

5. The cell preparation for treating brain tumors according to claim 4, wherein the cytosine deaminase gene and the uracil phosphoribosyltransferase gene are inserted into a region of a housekeeping gene or AAVS1 region of the pluripotent stem cells.

6. The cell preparation for treating brain tumors according to claim 5, wherein the housekeeping gene is a glyceraldehyde-3-phosphate dehydrogenase gene.

7. The cell preparation for treating brain tumors according to claim 3, wherein the cytosine deaminase gene and the uracil phosphoribosyltransferase gene are a gene structure, expression of which can be regulated artificially.

8. The cell preparation for treating brain tumors according to claim 7, wherein the gene structure is a gene structure expressed by addition of doxycycline.

9. The cell preparation for treating brain tumors according to claim 1, wherein the neural stem cells derived from pluripotent stem cells are neural stem cells obtained by performing the following step (1) and then performing the following step (2):
(1) differentiating pluripotent stem cells into neural stem cells,
(2) introducing a cytosine deaminase gene and a uracil phosphoribosyltransferase gene into the neural stem cells.

10. The cell preparation for treating brain tumors according to claim 1, wherein the pluripotent stem cells are iPS cells.

* * * * *